US009376694B2

(12) United States Patent
Shin et al.

(10) Patent No.: US 9,376,694 B2
(45) Date of Patent: Jun. 28, 2016

(54) METHOD FOR PREPARING OPTICALLY ACTIVE AMINO ACID USING COSUBSTRATE SHUTTLING OF TRANSAMINASE

(71) Applicant: INDUSTRY-ACADEMIC COOPERATION FOUNDATION, YONSEI UNIVERSITY, Seoul (KR)

(72) Inventors: Jong-Shik Shin, Gyeonggi-do (KR); Eul-Soo Park, Gyeonggi-do (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 14/347,174

(22) PCT Filed: Jul. 8, 2013

(86) PCT No.: PCT/KR2013/006028
§ 371 (c)(1),
(2) Date: Mar. 25, 2014

(87) PCT Pub. No.: WO2014/007588
PCT Pub. Date: Jan. 9, 2014

(65) Prior Publication Data
US 2015/0284750 A1    Oct. 8, 2015

(30) Foreign Application Priority Data
Jul. 6, 2012    (KR) .................. 10-2012-0074035

(51) Int. Cl.
*C12P 13/04*    (2006.01)
*C12P 13/14*    (2006.01)
*C12P 13/06*    (2006.01)
*C12P 13/08*    (2006.01)
*C12P 13/12*    (2006.01)
*C12P 13/20*    (2006.01)
*C12N 9/10*    (2006.01)

(52) U.S. Cl.
CPC .............. *C12P 13/14* (2013.01); *C12N 9/1096* (2013.01); *C12P 13/04* (2013.01); *C12P 13/06* (2013.01); *C12P 13/08* (2013.01); *C12P 13/12* (2013.01); *C12P 13/20* (2013.01); *C12Y 206/01018* (2013.01); *C12Y 206/01042* (2013.01); *Y02P 20/52* (2015.11)

(58) Field of Classification Search
None
See application file for complete search history.

(56) References Cited

U.S. PATENT DOCUMENTS

| 5,300,437 | A | * | 4/1994 | Stirling | C12N 9/1096 435/129 |
| 6,133,018 | A | * | 10/2000 | Wu | C12P 13/001 435/106 |
| 2009/0148899 | A1 | * | 6/2009 | Kawano | C12P 9/0004 435/69.1 |
| 2009/0246837 | A1 | | 10/2009 | Robins | |
| 2009/0298134 | A1 | * | 12/2009 | Fotheringham | C12P 13/001 435/106 |
| 2009/0325224 | A1 | | 12/2009 | Robins | |

FOREIGN PATENT DOCUMENTS

| KR | 1008186110000 | | 3/2008 |
| KR | 1010712740000 | | 9/2011 |
| WO | 00/23609 | | 4/2000 |
| WO | WO 00/23609 | * | 4/2000 |

OTHER PUBLICATIONS

Cho B. et al. Simultaneous Synthesis of Enantiomerically Pure (S) Amino Acids and (R) Amines Using Coupled Transaminase Reactions. Biotechnology and Bioengineering 81(7)783-789, Mar. 30, 2003.*
Abstract of Park, Eulsoo, et al., "One-Pot Conversion of L-Threonine into L-Homoalanine: Biocatalytic Production of an Unnatural Amino Acid from a Natrual One," Advanced Synthesis & Catalysis, Dec. 17, 2010, vol. 352, issue 18, pp. 3391-3398.
Galkin, Andrey, et al., "Synthesis of Optically Active Amino Acids from α-Keto Acids with *Escherichia coli* Cells Expressing Heterologous Genes," Applied and Environmental Microbiology, Dec. 1997, vol. 63, No. 12, pp. 4651-4656.
Cho. Byung-Kwan, et al., "Simultaneous Synthesis of Enantiomerically Pure (S)-Amino Acids and (R)-Amines Using Coupled Transaminase Reactions," Biotechnology and Bioengineering, Mar. 30, 2003, vol. 81, No. 7, pp. 783-789.
Mathew, Sam, et al., "ω-Transaminases for the Production of Optically Pure Amines and Unnatural Amino Acids;" ACS Catalysis, 201, vol. 2, pp. 993-1001.

* cited by examiner

*Primary Examiner* — Ralph Gitomer
(74) *Attorney, Agent, or Firm* — Duane Morris LLP; J. Rodman Steele, Jr.; Gregory M. Lefkowitz

(57) ABSTRACT

The present disclosure relates to a method for preparing an optically active amino acid using cosubstrate shuttling of transaminase. The method includes coupling a reaction of converting a keto acid to an amino acid by α-transaminase and a reaction of transferring an amino group of an amine substrate by ω-transaminase (TA) using an amino acid cosubstrate. The present disclosure allows production of various optically active amino acids with high purity and high efficiency by solving the low equilibrium constant problem of transaminase and is applicable to production of various optically active amino acids in industrial scale. Since the present disclosure allows easy production of various unnatural amino acids having high reactivity and stability, which are used as pharmaceutical precursors, it can be usefully employed in preparation of pharmaceuticals, food additives and various animal feeds.

8 Claims, 11 Drawing Sheets

Biphase reaction of L-tert-leucine (●) with trimethylpyruvate (○)
Monophase reaction of L-tert-leucine (▼) with trimethylpyruvate (▽)

Production of L-tert-leucine(○) from trimethylpyruvate(●)
(coupled enzyme reactions)

Concentration of L-homoalanine(▲) and 2-oxobutyrate(△)

ial Application No. PCT/KR2013/006028, filed Jul. 8, 2013, which claims priority to South Korean Patent Application No. 10-2012-0074035 filed Jul. 6, 2012, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on May 8, 2015, is named G1035-00901_SL.txt and is 17,474 bytes in size.

TECHNICAL FIELD

The present disclosure relates to a method for preparing an optically active amino acid using cosubstrate shuttling of transaminase, more particularly to a method for preparing an optically active amino acid with high conversion rate and high purity by coupling transamination by ω-transaminase with high equilibrium constant and a reaction by α-transaminase with low equilibrium constant using an amino acid cosubstrate and its keto acid that shuttle between the two reactions.

BACKGROUND ART

Optically active amino acids are important compounds used, for example, as intermediates of various pharmaceuticals. Especially, since unnatural amino acids which are highly valued as optically active intermediates are not metabolites producible by microorganisms, they cannot be produced by the production method of natural amino acids, such as fermentation. Although methods using metal catalysts are developed, they are uneconomical because transition metals are very expensive. Accordingly, an enzyme-based method may be economical and effective for production of optically active amino acids.

In this regard, α-transaminase is an industrially useful enzyme for production of optically active amino acids owing to fairly broad substrate specificity and high optical selectivity. However, its industrial utilization is limited because of low conversion rate due to small equilibrium constant.

Accordingly, for production of optically active amino acids using the enzyme-based method in industrial scale, it is necessary to overcome the low equilibrium constant of α-transaminase.

As existing methods for producing optically active amino acids using enzymes, Korean Patent Publication No. 10-2011-0047789 discloses a method for preparing an amino acid using microorganism-derived chain type transaminase and Korean Patent Publication No. 10-2008-0016287 discloses a method for producing an amino acid using β-transaminase.

DISCLOSURE

Technical Problem

The present disclosure is directed to, in order to overcome the low equilibrium constant of α-transaminase, providing a method for preparing an optically active amino acid with high purity by coupling with a ω-transaminase reaction with very large equilibrium constant using an amino acid cosubstrate exhibiting reactivity for the coupled reactions and a keto acid thereof.

Technical Solution

In one general aspect, the present disclosure provides a method for preparing an optically active amino acid by a cascade reaction, including coupling a reaction of converting a keto acid to an amino acid by α-transaminase and a reaction of transferring an amino group of an amine substrate by ω-transaminase (TA) using an amino acid cosubstrate.

Specifically, the α-transaminase may be branched-chain transaminase (BCTA), D-amino-acid transaminase (DATA), aromatic-amino-acid transaminase (AroTA), aspartate transaminase (AspTA) or alanine transaminase (ATA).

The amino acid cosubstrate may be any amino acid showing reactivity for both α-transaminase and ω-transaminase. More specifically, it may be selected from alanine, homoalanine, leucine, norvaline and norleucine. Most specifically, it may be alanine or homoalanine.

The keto acid may be any keto acid showing reactivity for α-transaminase. Specific examples include pyruvate, 2-oxobutyrate, 2-(3-hydroxy-1-adamantyl)-2-oxoethanoic acid, trimethylpyruvate, 3-methyl-2-oxobutyrate, 3-methyl-2oxopentanoic acid, 4-methyl-2-oxopentanoic acid, 2-oxopentanoic acid, 2-oxohexanoic acid, 2-oxooctanoic acid, fluoropyruvate, hydroxypyruvate, mercaptopyruvate, oxaloacetate, ketoglutarate, phenylglyoxylate, phenylpyruvate, 4-hydroxyphenylglyoxylate, 4-dimethyl-2oxopentanoic acid, 3-dimethyl-2-oxopentanoic acid, 3-ethyl-3-methyl-2-oxopentanoic acid, 5-dimethyl-2-oxohexanoic acid, etc.

The amine substrate may be any amine showing reactivity for ω-transaminase. Specific examples include benzylamine, methylbenzylamine, ethylbenzylamine, isopropylamine, 2-butylamine, 1-aminoindane, cyclopropylethylamine, 2-aminopentane, 3-methyl-2-butylamine, 1,3-dimethylbutylamine, 2-aminooctane, 1-methoxy-2-propylamine, 2-aminohexane, p-fluoromethylbenzylamine, mexiletine, 1-methyl-3-phenylpropylamine, etc. Specifically, it may be benzylamine, methylbenzylamine or isopropylamine.

The optically active amino acid produced by the method of the present disclosure may be optically pure amino acid in L- or D-form. Specifically, it may be alanine, homoalanine, norvaline, norleucine, 2-aminocaprylic acid, valine, leucine, isoleucine, tert-leucine, fluoroalanine, serine, cysteine, aspartate, glutamate, phenylglycine, phenylalanine, homophenylalanine, 4-hydroxyphenylalanine, 3-hydroxyadamantylglycine, neopentylglycine, 3-dimethyl-2-aminopentanoic acid, 3-ethyl-3-methyl-2-aminopentanoic acid or 5-dimethyl-2-aminohexanoic acid.

In an exemplary embodiment of the present disclosure, in the cascade reaction, the concentration of the amino acid cosubstrate may be 0.1-20% of the concentration of the keto acid substrate.

In an exemplary embodiment of the present disclosure, the cascade reaction may be conducted by further adding an organic solvent such as hexane if the reactivity of the ω-transaminase is inhibited by a ketone or an aldehyde.

In an exemplary embodiment of the present disclosure, the ratio of the α-transaminase (U/mL) and the ω-transaminase (U/mL) added for the cascade reaction may be 1:1-10.

In an exemplary embodiment of the present disclosure, the α-transaminase may be branched-chain transaminase isolated from *E. coli* and may have a DNA sequence of SEQ ID NO 7 and an amino acid sequence of SEQ ID NO 8.

In an exemplary embodiment of the present disclosure, the ω-transaminase may be one isolated from *Paracoccus denitrificans* and may have a DNA sequence of SEQ ID NO 9 and an amino acid sequence of SEQ ID NO 10.

In an exemplary embodiment of the present disclosure, the ω-transaminase may be one isolated from *Ochrobactrum anthropi* and may have a DNA sequence of SEQ ID NO 11 and an amino acid sequence of SEQ ID NO 12.

Advantageous Effects

The present disclosure allows production of various optically active amino acids with high purity by solving the low equilibrium constant problem of transaminase and is applicable to production of various optically active amino acids in industrial scale. Since the present disclosure allows easy production of various unnatural amino acids having high reactivity and stability, which are used as pharmaceutical precursors, it can be usefully employed in preparation of pharmaceuticals, food additives and various animal feeds.

BEST MODE FOR CARRYING OUT INVENTION

Figure 1:
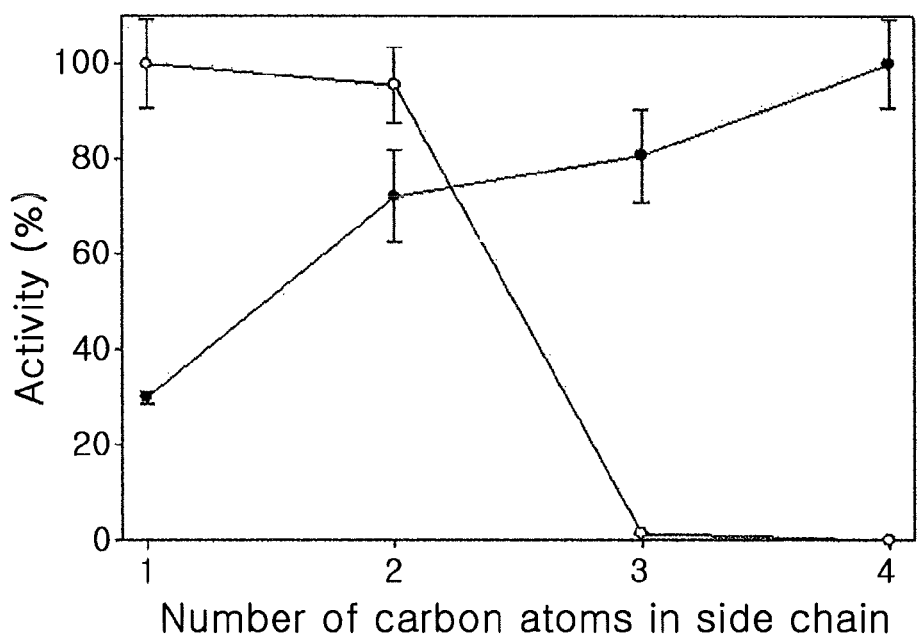
FIG. 1 describes selection of a cosubstrate based on the comparison of substrate specificity of branched-chain transaminase and ω-transaminase according to an exemplary embodiment of the present disclosure.

Hereinafter, the present disclosure is described in more detail.

Transaminase is a very important enzyme in amino acid metabolism. It catalyzes the transfer of an amino group between an amino acid and a keto acid with pyridoxal phosphate (PLP) as a coenzyme. Unlike other transaminases, ω-transaminase transfers an amino group of an amino acid or an amine compound having no carboxyl group, having the amino group at α-position, to an amino acceptor such as a keto acid or a ketone. Accordingly, ω-transaminase is a very useful enzyme in the production of optically active amine compounds.

The present disclosure relates to a method for preparing various optically active amino acids with high efficiency by coupling a reaction by α-transaminase such as branched-chain transaminase, D-amino-acid transaminase, aromatic-amino-acid transaminase, aspartate transaminase, alanine transaminase, etc. with a reaction by ω-transaminase using an amino acid cosubstrate and its keto acid that shuttle between the two reactions.

In an exemplary embodiment of the present disclosure, to provide a method for preparing various optically active amino acids with high purity and high efficiency by solving the low equilibrium constant problem of the conversion of a keto acid to an amino acid by α-transaminase, a reaction of converting a keto acid to an L-amino acid by branched-chain transaminase is coupled with a reaction of transferring an amino group of an amine substrate by (S)-selective ω-transaminase (ωTA) using an amino acid cosubstrate, as described in [Scheme 1].

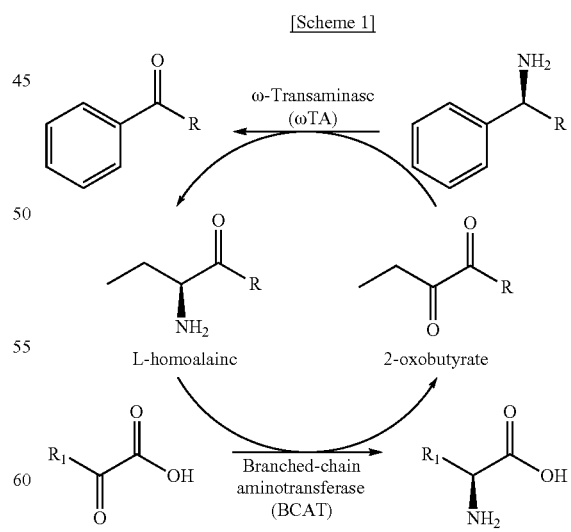

In another exemplary embodiment of the present disclosure, a reaction of converting a keto acid to a D-amino acid by D-amino-acid transaminase (DATA) is coupled with a reaction of transferring an amino group of an amine substrate by (R)-selective ω-transaminase (ωTA) using an amino acid cosubstrate, as described in [Scheme 2].

[Scheme 2]

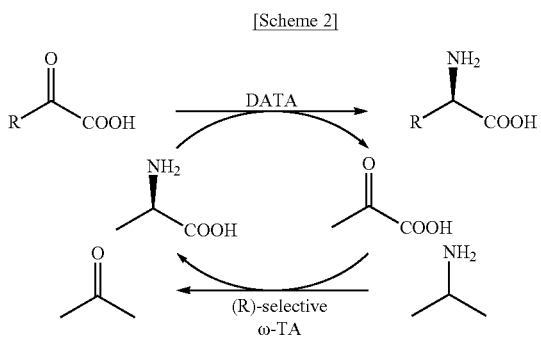

The amino acid cosubstrate that shuttles between the two reactions may be any amino acid which shows reactivity for both reactions and can be converted to its keto acid. Specifically, alanine, homoalanine, leucine, valine, norleucine, etc. may be used. More specifically, alanine or homoalanine having 1 or 2 carbon atoms may be used.

The keto acid may be any keto acid for which α-transaminase shows reactivity. Specific examples include pyruvate, 2-oxobutyrate, 2-(3-hydroxy-1-adamantyl)-2-oxoethanoic acid, trimethylpyruvate, 3-methyl-2-oxobutyrate, 3-methyl-2oxopentanoic acid, 4-methyl-2-oxopentanoic acid, 2-oxopentanoic acid, 2-oxohexanoic acid, 2-oxooctanoic acid, fluoropyruvate, hydroxypyruvate, mercaptopyruvate, oxaloacetate, ketoglutarate, phenylglyoxylate, phenylpyruvate, 4-hydroxyphenylglyoxylate, 4-dimethyl-2oxopentanoic acid, 3-dimethyl-2-oxopentanoic acid, 3-ethyl-3-methyl-2-oxopentanoic acid, 5-dimethyl-2-oxohexanoic acid, etc.

The amine substrate may be any amine for which ω-transaminase shows reactivity. Specific examples include benzylamine, methylbenzylamine, ethylbenzylamine, isopropylamine, 2-butylamine, 1-aminoindane, cyclopropylethylamine, 2-aminopentane, 3-methyl-2-butylamine, 1,3-dimethylbutylamine, 2-aminooctane, 1-methoxy-2-propylamine, 2-aminohexane, p-fluoromethylbenzylamine, mexiletine, 1-methyl-3-phenylpropylamine, etc. More specifically, benzylamine, methylbenzylamine or isopropylamine may be used.

The optically active amino acid produced by the method of the present disclosure may be an optically pure amino acid in L- or D-form, specifically, alanine, homoalanine, norvaline, norleucine, 2-aminocaprylic acid, valine, leucine, isoleucine, tert-leucine, fluoroalanine, serine, cysteine, aspartate, glutamate, phenylglycine, phenylalanine, homophenylalanine, 4-hydroxyphenylalanine, 3-hydroxyadamantylglycine, neopentylglycine, 3-dimethyl-2-aminopentanoic acid, 3-ethyl-3-methyl-2-aminopentanoic acid or 5-dimethyl-2-aminohexanoic acid.

In the cascade reaction according to the present disclosure, the concentration of the amino acid cosubstrate may be 0.1-20% of the concentration of the keto acid substrate. If the concentration of the cosubstrate is below 0.1% of the concentration of the keto acid substrate, conversion rate may be low. And, if the concentration of the cosubstrate is above 10% of the concentration of the keto acid substrate, it may be difficult to separate the produced amino acid. Hence, a concentration range of 0.1-10% is preferred.

And, the cascade reaction may be conducted by further adding an organic solvent, specifically hexane, to overcome inhibition of the reactivity of the ω-transaminase by the produced ketone or aldehyde.

MODE FOR CARRYING OUT INVENTION

Hereinafter, the present disclosure will be described in detail through examples. However, the following examples are for illustrative purposes only and it will be apparent to those of ordinary skill in the art that the scope of the present disclosure is not limited by the examples.

EXAMPLES

Example 1

Preparation of Recombinant DNA Consisting of Branched-Chain Transaminase DNA and Vector DNA from *E. coli*

*E. coli* cells cultured in a complete medium were centrifuged at 4,000 rpm for 10 minutes at 4° C. The supernatant was removed and the remaining cell pellet was lysed in 15 mL of a lysis buffer (15% sucrose, 25 mM EDTA, 25 mM Tris). The resultant was centrifuged at 4,000 rpm at 4° C. After discarding the supernatant and adding lysozyme (5 mg/mL in TSB buffer), the remainder was incubated at 37° C. for 10 minutes. After adding 1.2 mL of 0.5 M EDTA, the resulting solution was allowed to stand at 37° C. for 5 minutes. After adding 1 mL of 10% SDS, the resulting solution was kept at 70° C. and then kept in ice water for 10 minutes. After adding 2.5 mL of 5 M potassium acetate, the resulting solution was kept in ice water for 15 minutes. After adding a phenol-chloroform mixture (50:50) of the same volume as the solution and mixing for 30 minutes, the mixture was centrifuged at 4000 rpm for 10 minutes at 4° C. After adding chloroform corresponding to 0.5 time the volume of the obtained supernatant, the resulting solution was slowly agitated and centrifuged at 4000 rpm at 4° C. The supernatant was recovered and treated with 50 μg/mL RNase at 37° C. for 1 hour. Subsequently, after adding isopropanol of 0.8 volume equivalent and ethanol of 2.5 volume equivalents and agitating slowly, genomic DNA was collected using a heat-sealed Pasteur pipette, completely dried in a tube and then dissolved in TE buffer for further use.

Transaminase was acquired by PCR using the isolated genomic DNA as a template. The following primers were used.

```
                                          (SEQ ID NO 1)
Forward: 5'-ATCATGGAATTCATGACCACGAAGAAAGCT-3'

(SEQ ID NO 2)
Reverse: 5'-AAAAACTCGAGTTATTGATTAACTTGATCTAACCA-3'
```

The PCR product was treated with NdeI/BamHI restriction enzyme and the resulting fractions were ligated with pET24ma (acquired from Hiroshi Sakamoto, Paris) and pET23b (Novagen) to prepare a recombinant plasmid.

Example 2-(1)

Preparation of Recombinant DNA Consisting of ω-transaminase DNA and Vector DNA *Paracoccus denitrificans*

*Paracoccus denitrificans* was cultured in an LB broth (10 g/L peptone, 5 g/L yeast extract, 5 g/L sodium chloride, pH 7)

at 37° C. for 12 hours and genes expressing ω-transaminase were amplified from a single colony by PCR using synthetic DNA primers. The obtained DNA fragment was inserted into the expression vector DNA pET28a(+) using Nde1 and Xho1 restriction enzymes and ligase.

The following primers were used.

```
                                          (SEQ ID NO 3)
    Forward: 5'-GATATACATATGAACCAACCGCAAAGC-3'

(SEQ ID NO 4)
    Reverse: 5'-GTGGTGCTCGAGGGCCACCTCGGCAAA-3'
```

Example 2-(2)

Preparation of Recombinant DNA Consisting of ω-Transaminase DNA and Vector DNA
*Ochrobactrum anthropi*

*Ochrobactrum anthropi* was cultured in an LB broth (10 g/L peptone, 5 g/L yeast extract, 5 g/L sodium chloride, pH 7) at 37° C. for 12 hours and genes expressing ω-transaminase were amplified from a single colony by PCR using synthetic DNA primers. The obtained DNA fragment was inserted into the expression vector DNA pET28a(+) using Nde1 and Xho1 restriction enzymes and ligase.

The following primers were used.

```
                                          (SEQ ID NO 5)
Forward: 5'-GATATACCATGGNNACTGCTCAGCCAAACTCT-3'

(SEQ ID NO 6)
Reverse: 5'-CGAGTGCGGCCGTCCTGGTGAGGCTTGC-3'
```

Example 3

Overexpression of Enzymes from Transformed Bacteria and Purification

*E. coli* BL21(DE3) was transformed with the plasmids obtained in Examples 1, 2-(1) and 2-(2). The bacterium was cultured in 300 mL of an LB broth containing kanamycin and IPTG (final concentration=1 mM) was added to OD 0.5. After further culturing for at least 6 hours at 37° C., the bacterial cells were centrifuged at 10000×g for 20 minutes at 4° C. and resuspended in 15 mL of a resuspension buffer (50 mM Tris-HCl, 50 mM calcium chloride, 1 mM β-mercaptoethanol, 0.1 mM PMSF, 20 μM PLP, pH 7). After sonication on ice, followed by centrifugation at 17000×g for 30 minutes at 4° C., the supernatant was obtained as a crude extract.

The desired branched-chain transaminase and ω-transaminase were purified from the crude extract by affinity chromatography.

Branched-chain transaminase having a DNA sequence of SEQ ID NO 7 and an amino acid sequence of SEQ ID NO 8, ω-transaminase derived from *Paracoccus denitrificans* (Pd-wTA) having a DNA sequence of SEQ ID NO 9 and an amino acid sequence of SEQ ID NO 10, and ω-transaminase derived from *Ochrobactrum anthropi* having a DNA sequence of SEQ ID NO 11 and an amino acid sequence of SEQ ID NO 12 were obtained.

Example 4

Substrate Specificity of Branched-Chain Transaminase for Amino Acids and Conversion of Keto Acid to Optically Active Amino Acid Using Enzyme-Containing Crude Extract Reaction was conducted using the crude extract containing the branched-chain transaminase obtained in Example 3 and using various L-amino acids and keto acids described in [Table 1] as substrates. After adding 20 μL of the crude extract to 200 μL of a mixture of 20 mM L-amino acid, 20 mM keto acid and 50 mM potassium phosphate (pH 7.0), reaction was conducted at 37° C. for 30 minutes and the amount of produced L-amino acid was measured. The result is shown in [Table 1].

TABLE 1

| Amino acids | Keto acids | Production amount of L-amino acid (mM) |
|---|---|---|
| L-Glutamate | 2-Oxobutyrate | 4.2 |
| L-Homoalanine | α-Ketoglutarate | 0.1 |
| L-Valine | α-Ketoglutarate | 1.6 |
| L-Isoleucine | α-Ketoglutarate | 2.6 |
| L-tert-Leucine | α-Ketoglutarate | 0.06 |

Example 5

Substrate Specificity of Branched-Chain Transaminase for Amino Acids and Preparation of L-tert-leucine Using Enzyme-Containing Crude Extract Reaction was conducted using the crude extract containing the branched-chain transaminase obtained in Example 3 and using various trimethylpyruvate (keto acid of L-tert-leucine) as substrates. After adding 100 μL of the crude extract to 200 μL of a mixture of 20 mM trimethylpyruvate, 20 mM L-amino acid and 50 mM potassium phosphate (pH 7.0), reaction was conducted at 37° C. for 2 hours and the amount of produced L-tert-leucine was measured. The result is shown in [Table 2].

TABLE 2

| Keto acids | Amino acids | Production amount of L-tert-leucine (mM) |
|---|---|---|
| Trimethylpyruvate | Glutamate | 6.4 |
| Trimethylpyruvate | Homoalanine | 7.2 |
| Trimethylpyruvate | Valine | 7.8 |
| Trimethylpyruvate | Isoleucine | 9.2 |
| Trimethylpyruvate | Alanine | 0.8 |

Example 6

Substrate Specificity of Purified Branched-Chain Transaminase for Keto Acids and Conversion of Keto Acid to Optically Active Amino Acid Using Purified Enzyme Reaction was conducted using the branched-chain transaminase purified in Example 3 and using various L-amino acids and keto acids described in [Table 3] as substrates. After adding 10 μL of the purified enzyme (1 U/mL) to 100 μL of a mixture of 20 mM L-homoalanine, 20 mM keto acid and 50 mM potassium phosphate (pH 7.0), reaction was conducted at 37° C. for 7 hours and the amount of produced 2-oxobutyrate (keto acid of L-homoalanine) was measured. The result is shown in [Table 3].

When trimethylpyruvate and L-homoalanine were used as substrates, the equilibrium constant of the reaction by the branched-chain transaminase was very low at 0.16.

TABLE 3

| Keto acids (produced amino acids) | Amino acids | Concentration of 2-oxobutyrate [mM] |
|---|---|---|
| 3-Methyl-2-oxobutyrate (L-valine) | L-Homoalanine | 11.93 |
| 3-Methyl-2-oxoxpentanoic acid (L-isoleucine) | L-Homoalanine | 8.49 |
| 4-Methyl-2-oxopentanoic acid (L-leucine) | L-Homoalanine | 7.27 |
| 2-(3-Hydroxy-1-adamantyl)-2-oxoethanoic acid (3-hydroxyadamantyl glycine) | L-Homoalanine | 5.47 |
| Trimethylpyruvate (L-tert-leucine) | L-Homoalanine | 5.83 |

Example 7

Substrate Specificity of Purified Branched-Chain Transaminase for Amino Acids and Preparation of L-tert-leucine Using Purified Enzyme Reaction was conducted using the branched-chain transaminase purified in Example 3 and using various L-amino acids and trimethylpyruvate as substrates as described in [Table 4]. After adding 10 μL of the purified enzyme (6 U/mL) to 100 μL of a mixture of 20 mM trimethylpyruvate, 20 mM L-amino acid and 50 mM potassium phosphate (pH 7.0), reaction was conducted at 37° C. for 6 hours and the amount of produced L-tert-leucine was measured. The result is shown in [Table 4].

TABLE 4

| Keto acids | L-Amino acids | Concentration of L-tert-leucine (mM) | | |
|---|---|---|---|---|
| Trimethylpyruvate | L-Alanine | 2.24 | 2.07 | 2.23 |
| Trimethylpyruvate | L-Homoalanine | 5.57 | 4.43 | 5.71 |
| Trimethylpyruvate | L-Valine | 6.31 | 5.04 | 6.23 |
| Trimethylpyruvate | L-Norvaline | 6.31 | 5.34 | 6.06 |
| Trimethylpyruvate | L-Norleucine | 5.90 | 5.48 | 5.55 |
| Trimethylpyruvate | L-Leucine | 6.71 | 6.32 | 7.06 |
| Trimethylpyruvate | L-Isoleucine | 7.79 | 7.48 | 6.51 |

Example 8

Substrate Specificity of Purified ω-transaminase for Amino Acids and Preparation of L-glycine Using Purified ω-transaminase Reaction was conducted using the ω-transaminase purified in Example 3 and using various L-amino acids and trimethylpyruvate as substrates as described in [Table 5]. After adding 10 μL of the purified enzyme (5 U/mL) to 100 μL of a mixture of 20 mM glyoxylate, 20 mM L-amino acid and 50 mM potassium phosphate (pH 7.0), reaction was conducted at 37° C. for 6 hours and the amount of produced L-glycine was measured. The reaction was conducted 3 times and the result was compared with that of the ω-transaminase derived from *Ochrobactrum anthropi*. The result is shown in [Table 5].

TABLE 5

| Amino acceptors | Amino donors | Concentration of L-glycine (mM) | | | |
|---|---|---|---|---|---|
| | | PdwTA | | OawTA | |
| Glyoxylate | L-Alanine | 13.92 | 13.31 | 11.61 | 11.73 |
| Glyoxylate | L-Homoalanine | 12.56 | 13.31 | 11.26 | 4.97 |
| Glyoxylate | L-Valine | 0.18 | 0.20 | 0.17 | 0.00 |
| Glyoxylate | L-Norvaline | 13.43 | 14.29 | 14.12 | 0.36 |
| Glyoxylate | L-Norleucine | 13.41 | 12.97 | 12.59 | 0.28 |
| Glyoxylate | L-Leucine | 7.93 | 7.95 | 5.71 | 0.00 |
| Glyoxylate | L-Isoleucine | 0.00 | 0.00 | 0.00 | 0.00 |

Example 9

Substrate Specificity of Purified ω-transaminase for Keto Acids and Conversion to Optically Active Amino Acid Using Purified ω-transaminase Reaction was conducted using the ω-transaminase purified in Example 3 and using various keto acids and amine as substrates as described in [Table 6]. After adding 10 μL of the purified enzyme (6 U/mL) to 100 μL of a mixture of 20 mM keto acid, 20 mM (S)-α-methylbenzylamine and 50 mM potassium phosphate (pH 7.0), reaction was conducted at 37° C. for 6 hours and the amount of produced acetophenone (deaminated ketone of (S)-α-methylbenzylamine) was measured. The result was compared with that of the ω-transaminase derived from *Ochrobactrum anthropi*. The result is shown in [Table 6].

TABLE 6

| Keto acids | Produced amino acids | Amine | Concentration of acetophenone (mM) | |
|---|---|---|---|---|
| | | | PdwTA | OawTA |
| Pyruvate | L-Alanine | (S)-α-MBA | 5.18 | 4.84 |
| 2-Oxobutyrate | L-Homoalanine | (S)-α-MBA | 5.03 | 5.05 |
| 3-Methyl-2-oxobutyrate | L-Valine | (S)-α-MBA | 0.00 | 0.00 |
| 2-Oxopentanoic acid | L-Norvaline | (S)-α-MBA | 5.24 | 3.45 |
| 2-Oxohexanoic acid | L-Norleucine | (S)-α-MBA | 5.22 | 3.07 |
| 4-Methyl-2-oxopentanoic acid | L-Leucine | (S)-α-MBA | 4.99 | 0.03 |
| 3-Methyl-2-oxopentanoic acid | L-Isoleucine | (S)-α-MBA | 0.00 | 0.00 |

Example 10

Substrate Specificity of Purified ω-transaminase for Keto Acids in Initial Stage of Reaction and Conversion to Optically Active Amino Acid Using Purified ω-transaminase Reaction was conducted using the ω-transaminase purified in Example 3 and using various keto acids and amine as substrates as described in [Table 7]. After adding 10 μL of the purified enzyme (1 U/mL) to 100 μL of a mixture of 20 mM keto acid, 20 mM (S)-α-methylbenzylamine and 50 mM potassium phosphate (pH 7.0), reaction was conducted at 37° C. for 10 minutes and the amount of produced acetophenone (deaminated ketone of (S)-α-methylbenzylamine) was measured. The result was compared with that of the ω-transaminase derived from *Ochrobactrum anthropi*. The result is shown in [Table 7].

TABLE 7

| Keto acids | OawTA | PdwTA |
| --- | --- | --- |
| Gyloxylate | 1.733 | 1.076 |
| Pyruvate | 1.284 | 1.216 |
| 2-Oxobutyrate | 0.173 | 0.821 |
| β-Hydroxypyruvate | 0.183 | 0.066 |
| Mercaptopyruvate | 0.012 | 0.008 |
| Fluoropyruvate | 0.554 | 0.339 |
| Bromopyruvate | 0.010 | −0.001 |
| 2-Oxopentanoic acid | 0.378 | 1.332 |
| 4-Methyl-2-oxopentanoic acid | 0.005 | 0.175 |
| 2-Ketohexanoic acid | 0.006 | 0.713 |

Example 11

Selection of Cosubstrate Based on Comparison of Substrate Specificity of Branched-Chain Transaminase and ω-transaminase From the comparison of substrate specificity of the two enzymes obtained in Examples 4-10, it was found out that the branched-chain transaminase exhibits higher activity as the number of carbon atoms in the side chain of an amino acid is larger whereas the ω-transaminase exhibits lower activity as the number of carbon atoms in the side chain of an amino acid is larger.

Accordingly, L-homoalanine, the only substrate showing good activity for the two enzymes, was selected as a cosubstrate that will shuttle between the reactions by the two transaminases. This is graphically illustrated in FIG. 1.

Example 12

Determination of Optimal Concentration of Cosubstrate for Coupled Enzyme Reactions by Branched-Chain Transaminase and ω-transaminase and Production of L-tert-leucine by Coupled Enzyme Reactions The change in the production amount of L-tert-leucine was monitored while increasing the concentration of L-homoalanine, which was determined as the cosubstrate of branched-chain transaminase and ω-transaminase in Example 11, with the concentrations of trimethylpyruvate (substrate of branched-chain transaminase) and benzylamine (substrate of ω-transaminase) fixed.

Figure 2:
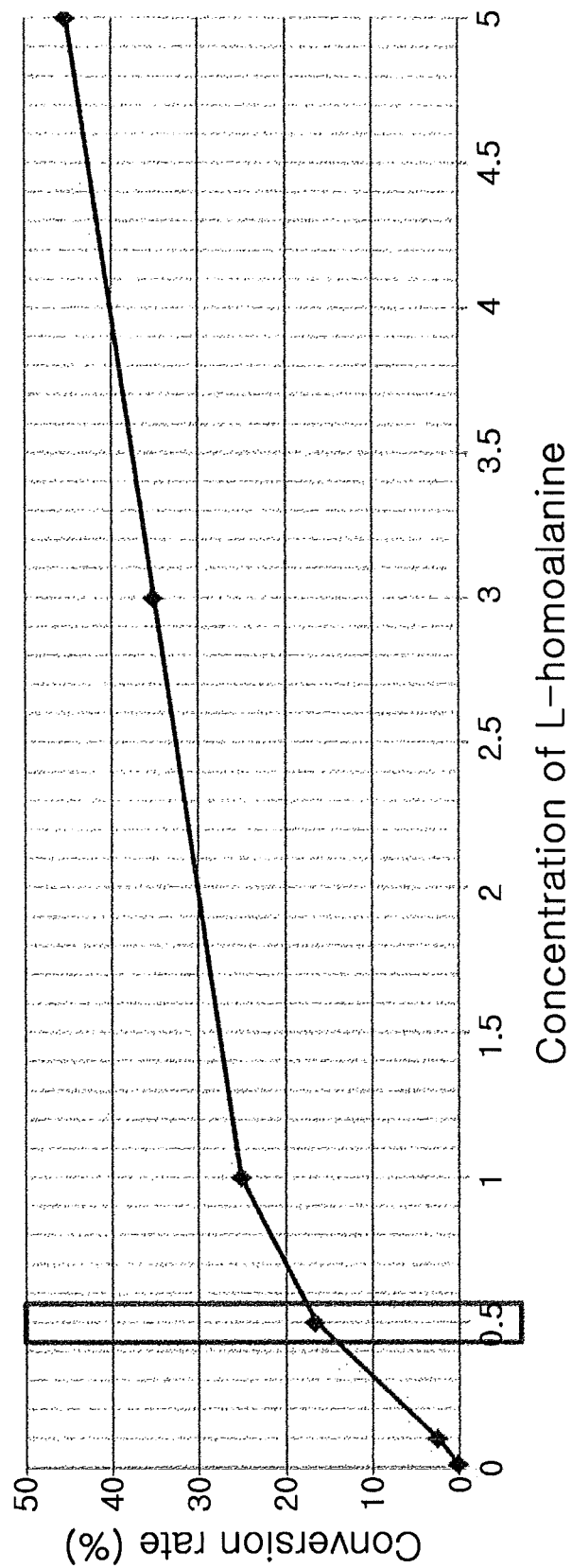
FIG. 2 shows a result of investigating the optimal concentration of a cosubstrate in coupled enzyme reactions by branched-chain transaminase and ω-transaminase transaminase according to an exemplary embodiment of the present disclosure.

The rate of conversion from trimethylpyruvate to L-tert-leucine was measured while conducting reactions at 37° C. for 7 hours using 100 μL of a mixture of 5 mM trimethylpyruvate, 5 mM benzylamine, 5 mM pyridoxal 5'-phosphate (PLP), 50 mM potassium phosphate, 0.1 U/mL branched-chain transaminase and 0.1 U/mL ω-transaminase and changing the concentration of the cosubstrate L-homoalanine from 0 mM to 5 mM. Since the conversion rate did not increase significantly above the cosubstrate concentration of 0.5 mM, which is 10% of the substrate concentration, the optimal concentration of the cosubstrate was determined as 10% of that of the keto acid substrate. The result is shown in FIG. 2.

Example 13

Production of L-tert-leucine by Coupled Enzyme Reactions while Varying ω-transaminase Concentration with Branched-Chain Transaminase Concentration Fixed The change in conversion rate was monitored while conducting coupled enzyme reactions by varying ω-transaminase concentration with branched-chain transaminase concentration fixed. The rate of conversion to L-tert-leucine with time was monitored while conducting reactions using 20 mM trimethylpyruvate, 2 mM L-homoalanine, 30 mM benzylamine, 0.1 mM PLP, 50 mM potassium phosphate (pH 7) and 0.6 U/mL branched-chain transaminase and varying the concentration of ω-transaminase at 5, 50 and 500 mU/mL.

Figure 3:
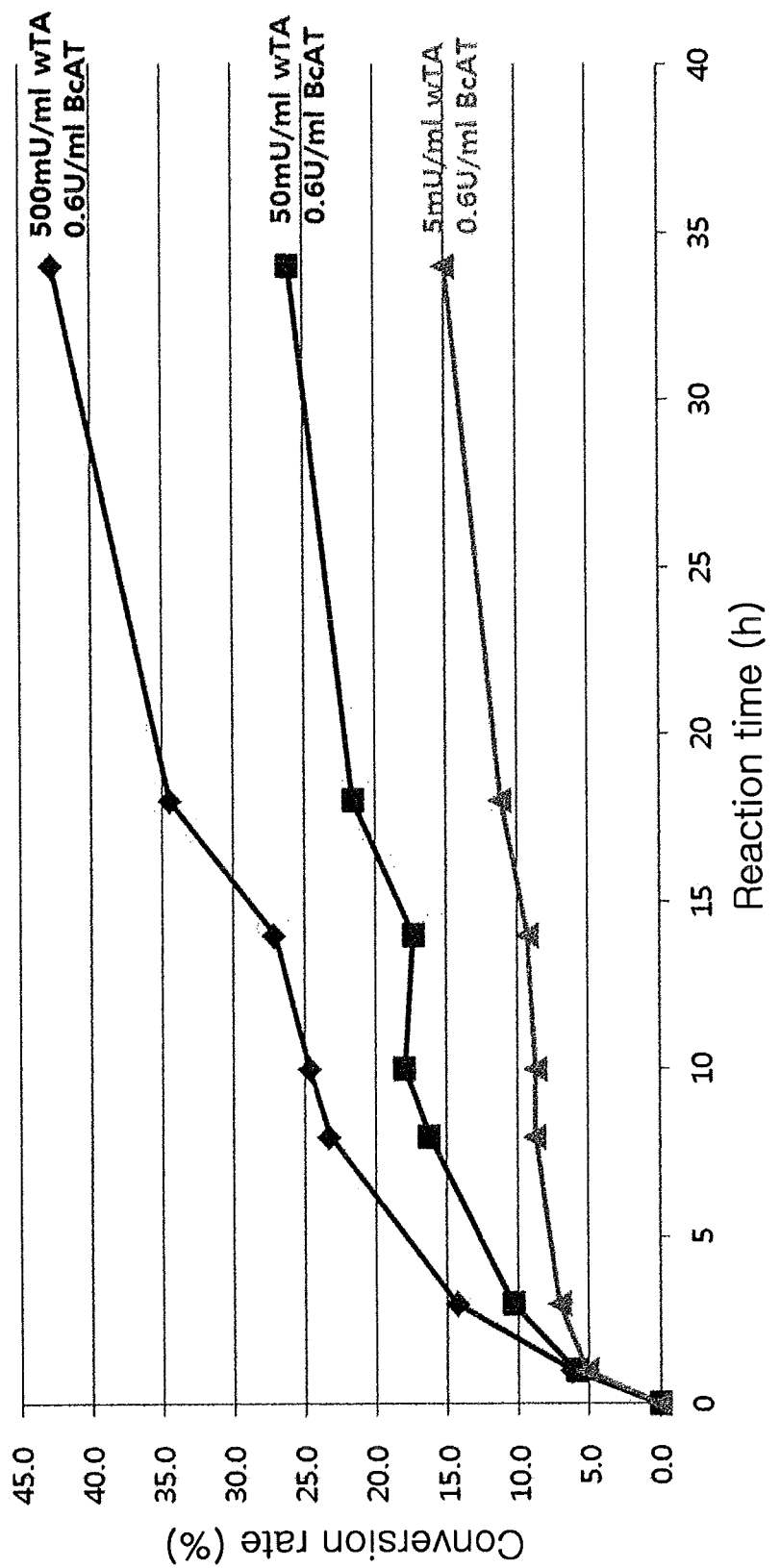
FIG. 3 shows a result of conducting coupled enzyme reactions while varying the concentration of ω-transaminase with the concentration of branched-chain transaminase fixed according to an exemplary embodiment of the present disclosure.

Up to 5% conversion rate, i.e. when 1 mM cosubstrate was consumed, there was no difference in the conversion rate depending on the ω-transaminase concentration. However, a very significant difference in the conversion rate was observed at higher conversion rate depending on the ω-transaminase concentration. This suggests that the shuttling effect of the cosubstrate by ω-transaminase is very effective in overcoming the low equilibrium constant of the branched-chain transaminase reaction. The result is shown in FIG. 3.

Example 14

Figure 4:
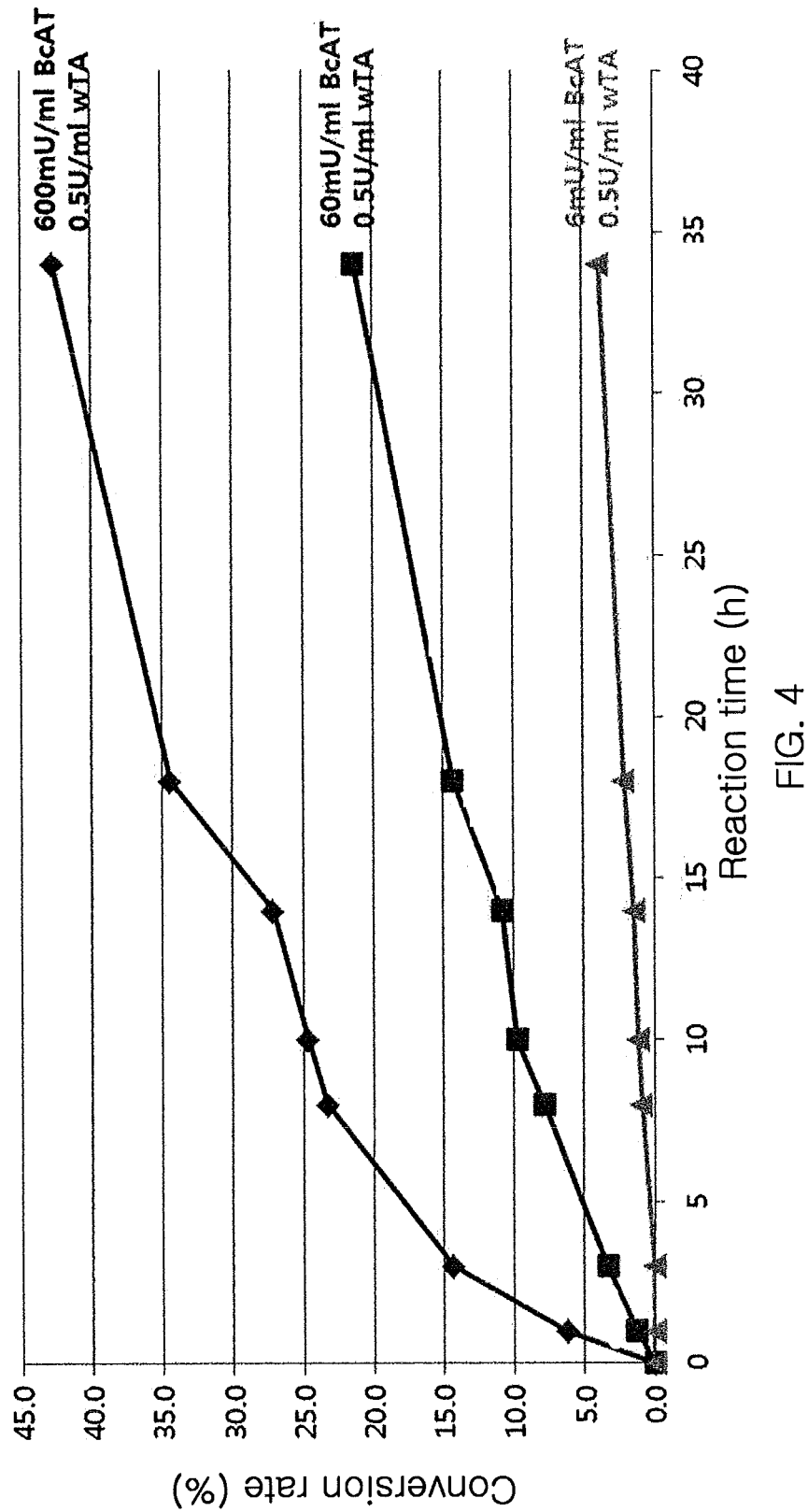
FIG. 4 shows a result of conducting coupled enzyme reactions while varying the concentration of branched-chain transaminase with the concentration of ω-transaminase fixed according to an exemplary embodiment of the present disclosure.

Production of L-tert-leucine by Coupled Enzyme Reactions while Varying Branched-Chain Transaminase with ω-transaminase Concentration Fixed The change in conversion rate was monitored while conducting coupled enzyme reactions by varying branched-chain transaminase concentration with ω-transaminase concentration fixed. The rate of conversion to L-tert-leucine with time was monitored while conducting reactions using 20 mM trimethylpyruvate, 2 mM L-homoalanine, 30 mM benzylamine, 0.1 mM PLP, 50 mM potassium phosphate (pH 7) and 0.5 U/mL ω-transaminase and varying the concentration of branched-chain transaminase at 6, 60 and 600 mU/mL. Since the cosubstrate was shuttled by the ω-transaminase, a large difference in the conversion rate was observed depending on the branched-chain transaminase concentration from the early stage of reaction. The result is shown in FIG. 4.

Example 15

Production of L-tert-leucine by Coupled Enzyme Reactions while Adding Organic Solvent and Using Racemic Cosubstrate to Overcome Inhibition of ω-transaminase Reaction The change in conversion rate was monitored while conducting coupled enzyme reactions by adding hexane and using racemic cosubstrate in order to overcome inhibition of ω-transaminase reaction by the product. L-tert-Leucine was in a biphase system using 1 mL of a mixture of 20 mM trimethylpyruvate, 2 mM L-homoalanine, 30 mM benzylamine, 0.1 mM PLP, 50 mM potassium phosphate (pH 7), 1.4 U/mL branched-chain transaminase and 1.9 U/mL ω-transaminase and adding 3 mL of hexane. The change in conversion rate was monitored while changing the concentration of the racemic cosubstrate from 2 mM to 4 mM.

Figure 5:
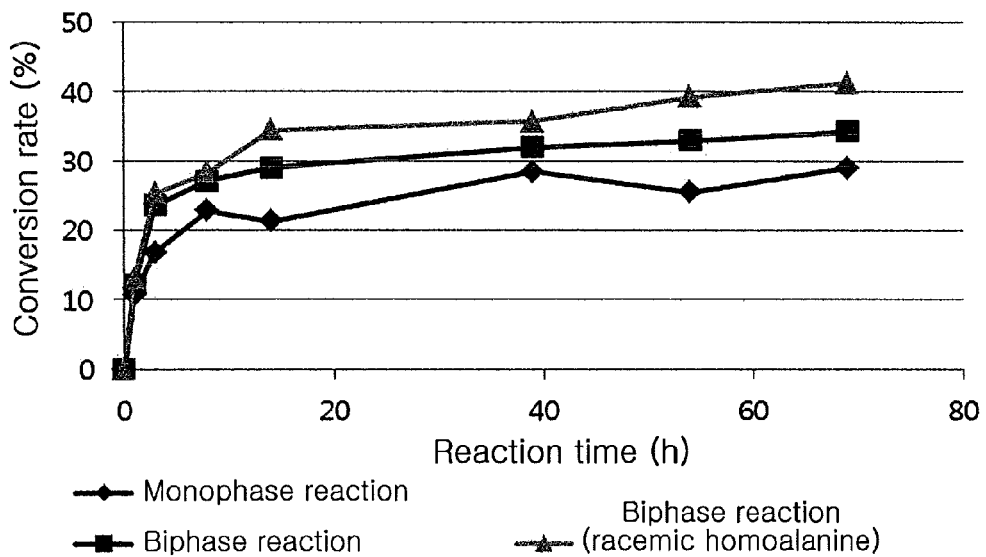
FIG. 5 shows a result of conducting coupled enzyme reactions while adding an organic solvent for overcoming inhibition of ω-transaminase reaction and using a racemic cosubstrate according to an exemplary embodiment of the present disclosure.

The addition of hexane resulted in increased conversion rate because of the production of aldehyde which inhibits the reaction was suppressed. Also, the conversion to L-tert-leucine by the coupled enzyme reactions was not affected at all although the racemic cosubstrate was used. The result is shown in FIG. 5.

Example 16

Figure 6:
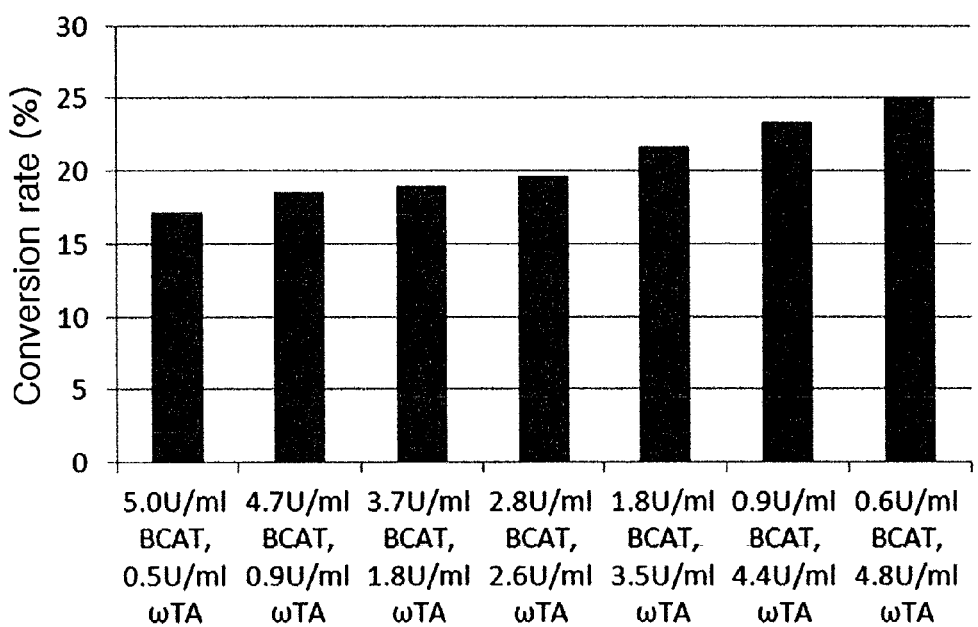
FIG. 6 shows a result of conducting coupled enzyme reactions while changing the ratio of ω-transaminase and branched-chain transaminase within a restricted volume ratio according to an exemplary embodiment of the present disclosure.

Production of L-tert-leucine Depending on Ratio of ω-transaminase and Branched-Chain Transaminase within Limited Volume The change in conversion rate of L-tert-leucine depending on the ratio of branched-chain transaminase and ω-transaminase within limited volume was monitored. The change in conversion rate to L-tert-leucine was monitored while conducting reactions at 37° C. for 19 hours using 1 mL of a mixture of 20 mM trimethylpyruvate, 4 mM D/L-homoalanine, 30 mM benzylamine, 0.1 mM PLP and 50 mM potassium phosphate (pH 7) while varying the ratio of branched-chain transaminase and ω-transaminase. The best conversion rate was achieved when the ratio of the branched-chain transaminase to the ω-transaminase was 1:8 (U/mL). The result is shown in FIG. 6.

Example 17

Production of L-tert-leucine by Coupled Enzyme Reactions with Addition of Organic Solvent Using the enzyme ratio that showed the best conversion rate in Example 16, L-tert-leucine was produced by coupled biphase reactions by adding an organic solvent. The conversion rate was compared while conducting reactions using 1 mL of a mixture of 20 mM trimethylpyruvate, 4 mM D/L-homoalanine, 30 mM benzylamine, 0.1 mM PLP, 50 mM potassium phosphate (pH 7), 0.6 U/mL branched-chain transaminase and 4.8 U/mL ω-transaminase 1 mL, with or without (monophase) 3 mL of hexane added.

Figure 7:
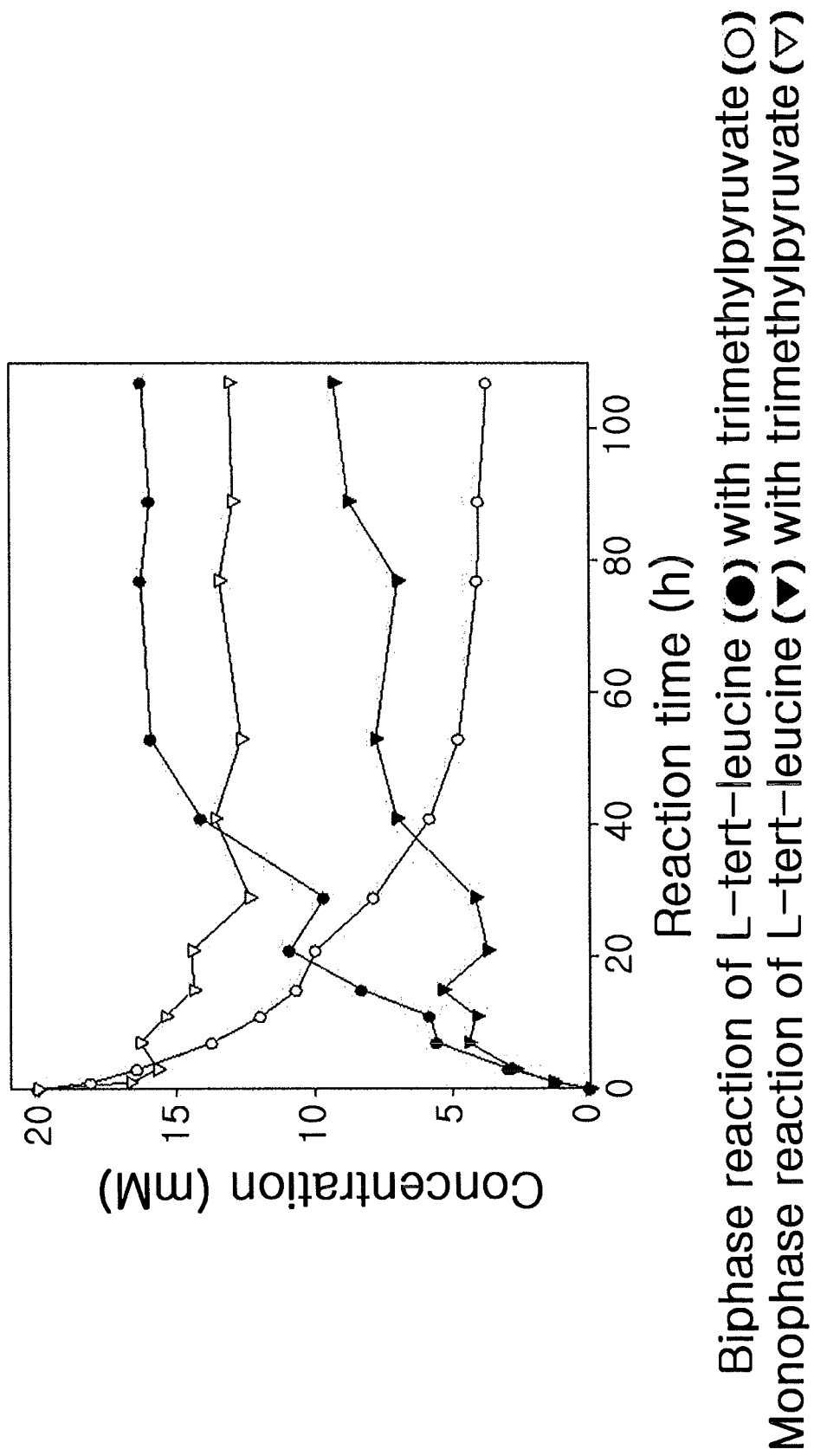
FIG. 7 and FIG. 8 show a result of conducting coupled enzyme reactions while adding an organic solvent according to an exemplary embodiment of the present disclosure.
Figure 8:
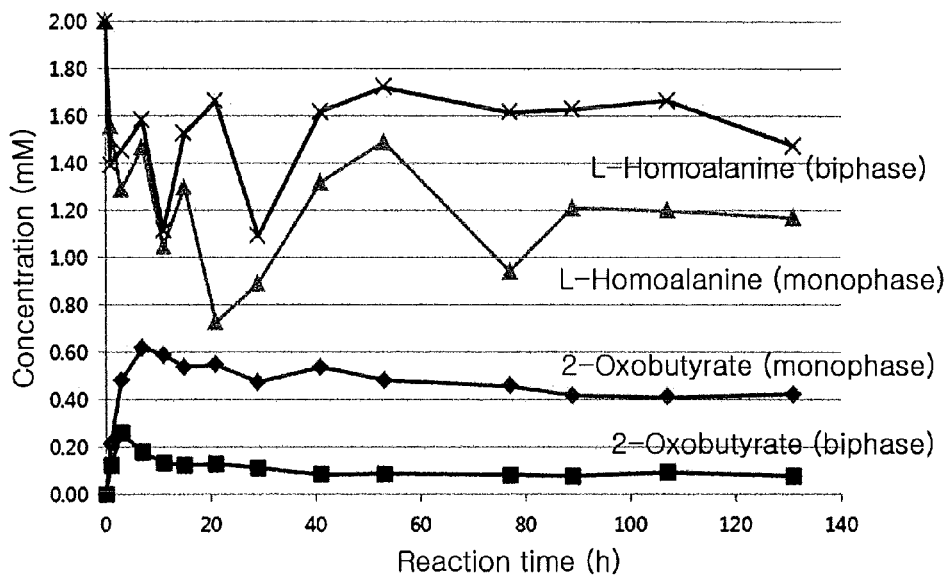

The addition of the organic solvent resulted in the increased conversion to L-tert-leucine close to 200%. When the concentrations of the cosubstrate and its keto acid (2-oxobutyrate) in the reaction mixture were monitored, it was found out that the cosubstrate concentration was continuously maintained close to the initial substrate concentration owing to the addition of the organic solvent, and this resulted in the improved conversion rate to L-tert-leucine. The result is shown in FIG. 7 and FIG. 8.

Example 18

Production of L-tert-leucine by Coupled Enzyme Reactions by ω-transaminase Depending on Amine Substrate The change in conversion rate to L-tert-leucine was monitored while conducting coupled enzyme reactions using benzylamine or (S)-α-methyl benzylamine as an amine substrate of ω-transaminase. The change in conversion rate was monitored while conducting reactions at 37° C. using 1 mL of a mixture of 20 mM trimethylpyruvate, 4 mM D/L-homoalanine, 30 mM amine substrate, 0.1 mM PLP, 50 mM potassium phosphate (pH 7), 0.6 U/mL branched-chain transaminase and 0.5 U/mL ω-transaminase.

Figure 9:
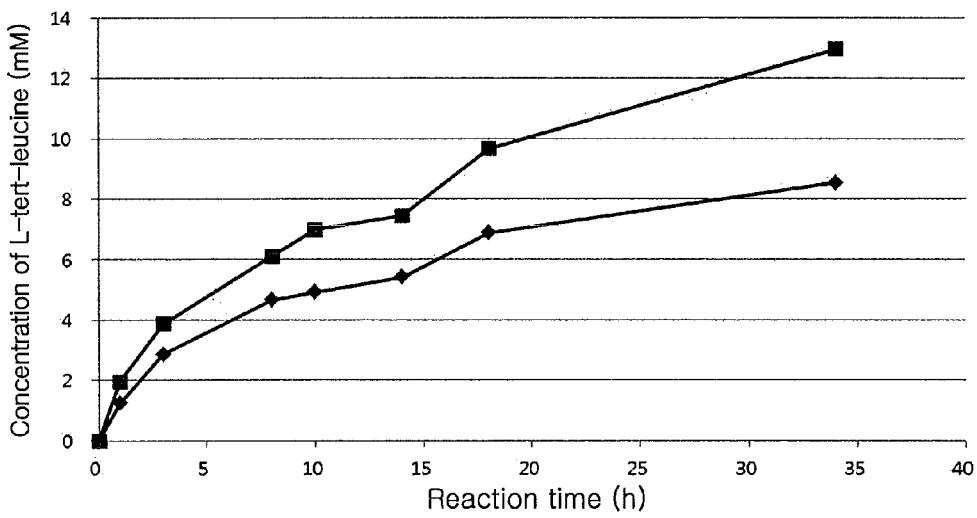
FIG. 9 shows a result of conducting coupled enzyme reactions while varying the amine substrate of ω-transaminase according to an exemplary embodiment of the present disclosure.

When (S)-α-methylbenzylamine was used as the amine substrate of ω-transaminase, the conversion rate was improved by 150% as compared to when benzylamine was used as the amine substrate. The result is shown in FIG. 9.

Example 19

Production of L-tert-leucine by Coupled Enzyme Using Racemic Amine Substrate

L-tert-Leucine was produced by coupled enzyme using a racemic amine substrate. L-tert-Leucine was produced at 37° C. by conducting reactions using 1 mL of a mixture of 20 mM trimethylpyruvate, 4 mM D/L-homoalanine, 60 mM rac-α-methylbenzylamine, 0.1 mM PLP, 50 mM potassium phosphate (pH 7), 0.6 U/mL branched-chain transaminase and 4.8 U/mL ω-transaminase while adding 6 mL of hexane.

Figure 10:
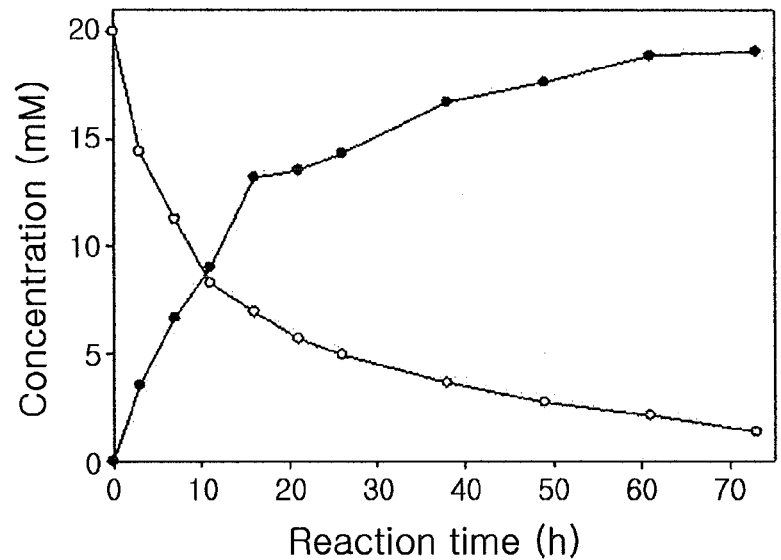
FIGS. 10-12 shows a result of producing L-tert-leucine through coupled enzyme reactions using a racemic amine substrate according to an exemplary embodiment of the present disclosure.
Figure 11:
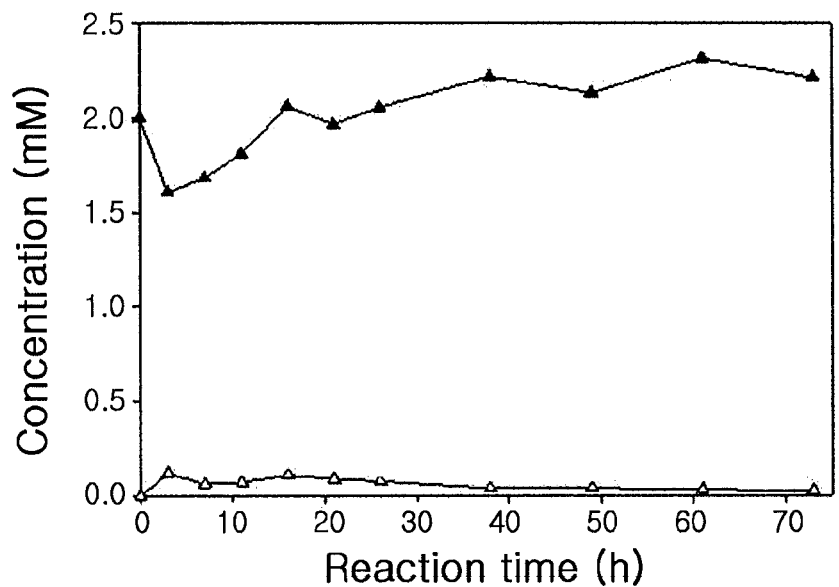
Figure 12:
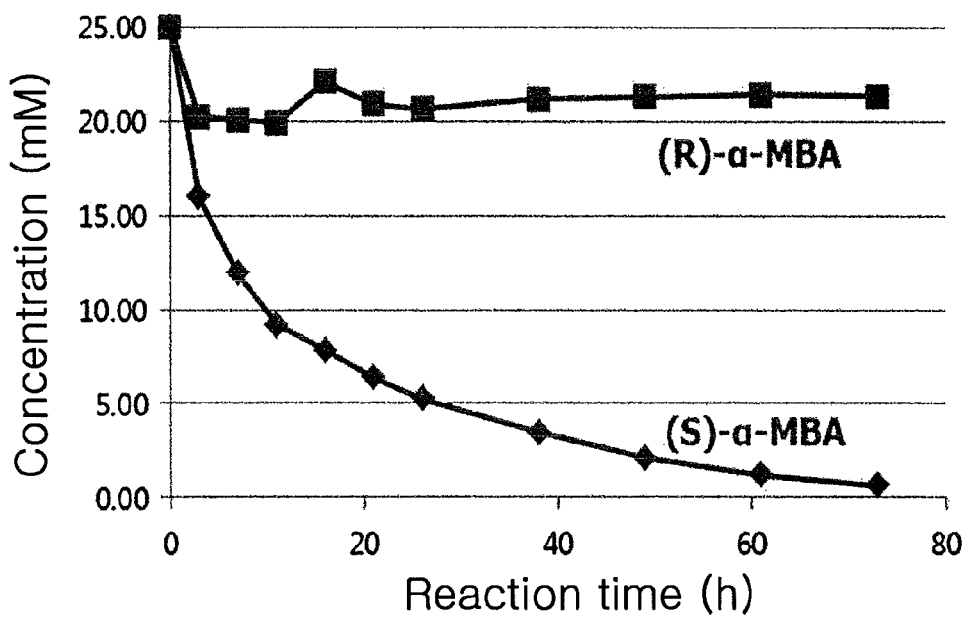

Optically active L-tert-leucine was produced by the coupled enzyme reactions with a conversion rate of 95.4%. The conversion from trimethylpyruvate to L-tert-leucine owing to shuttling of the cosubstrate was confirmed from the analysis of the cosubstrate and its keto acid during the coupled enzyme reactions. Also, production of (R)-α-methylbenzylamine by a selective reaction by ω-transaminase was confirmed. The result is shown in FIG. 10, FIG. 11 and FIG. 12.

Example 20

Production of L-3-hydroxyadamantylglycine by Coupled Enzyme Reactions

L-3-Hydroxyadamantylglycine was produced by coupled enzyme reactions using a racemic amine substrate. L-3-Hydroxyadamantylglycine was produced at 37° C. by conducting reactions using 1 mL of a mixture of 20 mM 2-(3-hydroxy-1-adamantyl)-2-oxoethanoic acid, 4 mM D/L-homoalanine, 60 mM rac-α-methylbenzylamine, 0.1 mM PLP, 50 mM potassium phosphate (pH 7), 0.6 U/mL branched-chain transaminase and 4.8 U/mL ω-transaminase while adding 6 mL of hexane.

Figure 13:
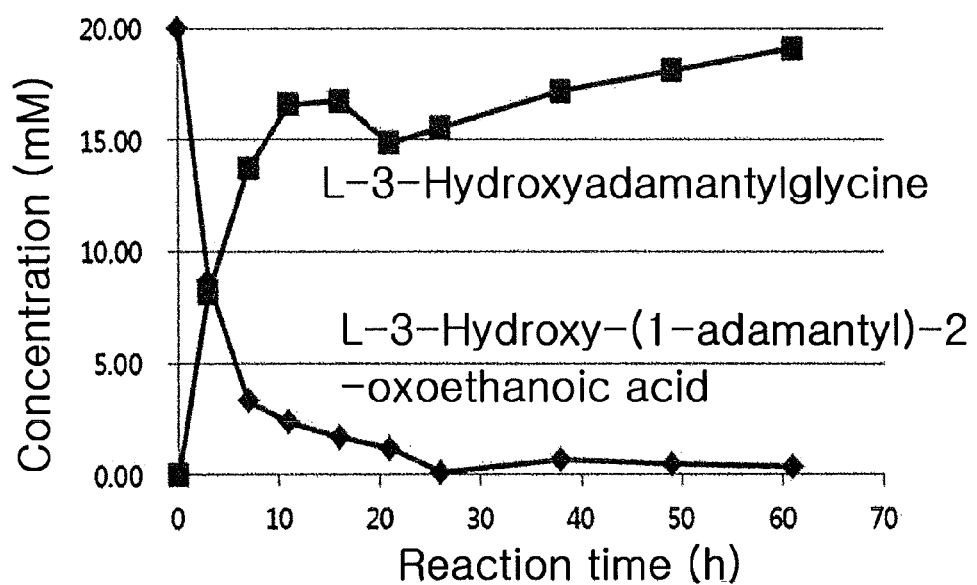
FIGS. 13-15 shows a result of producing L-3-hydroxyadamantylglycine through coupled enzyme reactions according to an exemplary embodiment of the present disclosure.
Figure 14:
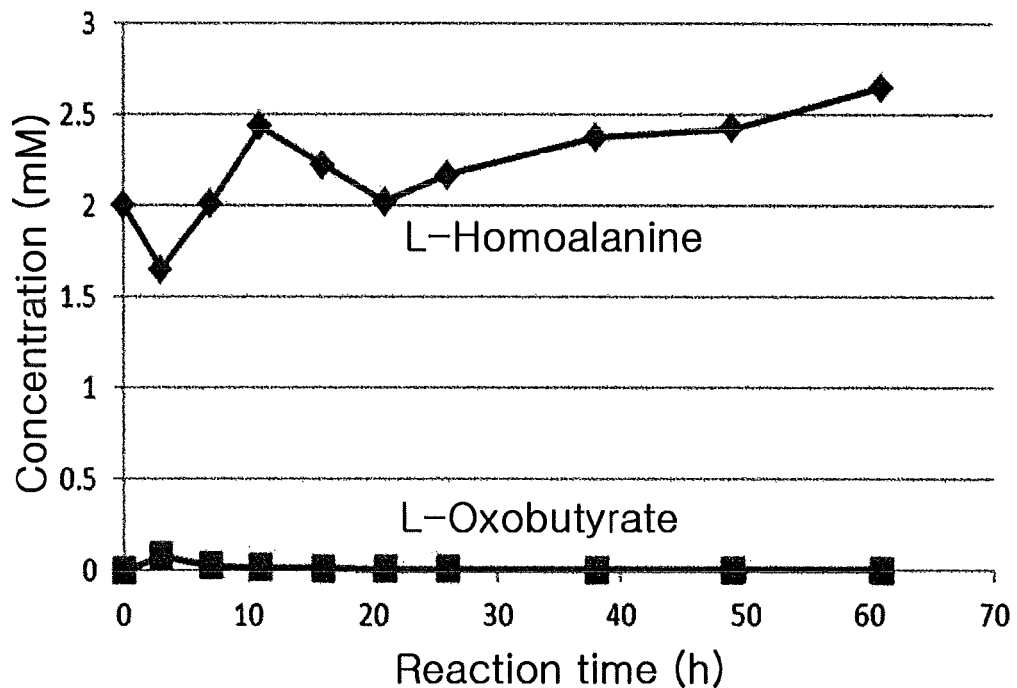
Figure 15:
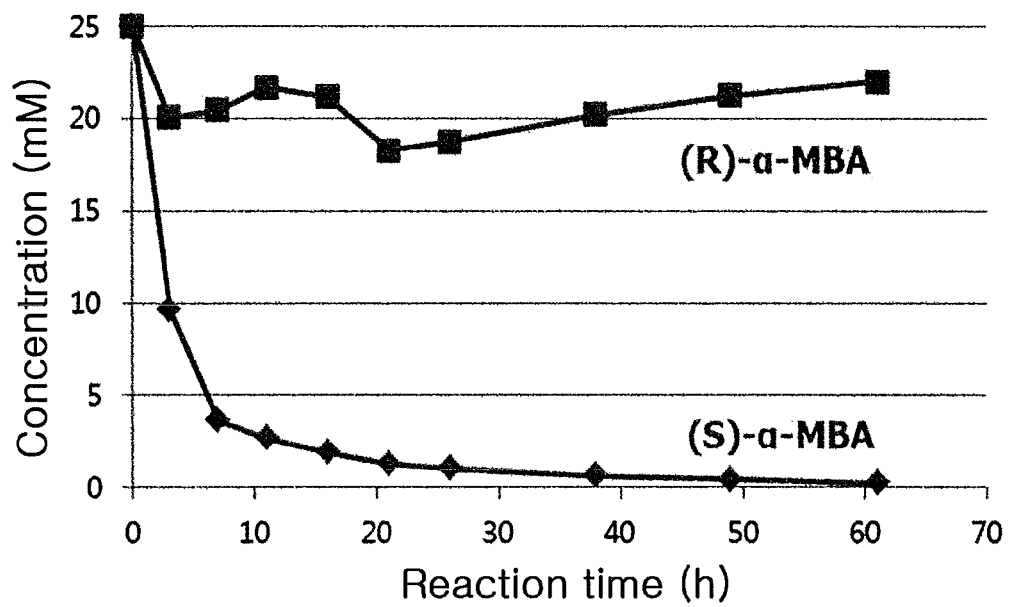

Optically active L-3-hydroxyadamantylglycine was produced by the coupled enzyme reactions with a conversion rate of 98.15%. The conversion from 2-(3-hydroxy-1-adamantyl)-2-oxoethanoic acid to L-3-hydroxyadamantylglycine owing to shuttling of the cosubstrate was confirmed from the analysis of the cosubstrate and its keto acid during the coupled enzyme reactions. Also, production of (R)-α-methylbenzylamine by a selective reaction by ω-transaminase was confirmed. The result is shown in FIG. 13, FIG. 14 and FIG. 15.

Example 21

Production of Various Unnatural Amino Acids and Branched-Chain Amino Acids by Coupled Enzyme Reactions Various unnatural amino acids and branched-chain amino acids were produced by coupled enzyme reactions. Unnatural amino acids and branched-chain amino acids were produced at 37° C. by conducting reactions using 1 mL of a mixture of 20 mM keto acid, 4 mM D/L-homoalanine, 60 mM rac-α-methylbenzylamine, 0.1 mM PLP, 50 mM potassium phosphate (pH 7), 0.6 U/mL branched-chain transaminase and 4.8 U/mL ω-transaminase while adding 6 mL of hexane.

As keto acids for the production of the optically active amino acids, 2-oxopentanoate was used for L-norvaline, 2-oxo-3-methylbutyrate for L-valine, 2-oxohexanoate for L-norleucine, and 2-oxo-4-pentanoate for L-leucine. The various unnatural amino acids and branched-chain amino acids were produced by the coupled enzyme reactions with a conversion rate of 90% or higher. The result is shown in [Table 8].

TABLE 8

| | Keto acid (mM) | L-Amino acid (mM) | D-Amino acid (mM) | S-MBA (mM) | R-MBA (mM) | MBA ee (%) | Reaction time (hr) |
|---|---|---|---|---|---|---|---|
| Norvaline | 0 | 19.93 | 0.00 | 4.60 | 21.61 | 64.89 | 76 |
| Valine | 1.58 | 21.25 | 0.02 | 3.56 | 21.10 | 72.02 | 40 |
| Norleucine | 0 | 19.57 | 0.01 | 3.35 | 20.98 | 72.46 | 40 |
| leucine | 0 | 19.73 | 0.02 | 3.94 | 20.72 | 68.06 | 53 |

Example 22

Production of L-tert-leucine by Coupled Enzyme Reactions Using ω-transaminase Derived from *Ochrobactrum anthropi* and Using Isopropylamine as Amine Substrate of ω-transaminase Since the ω-transaminase derived from *Ochrobactrum anthropi* exhibits stronger activity for isopropylamine than that derived from *Paracoccus denitrificans*, L-tert-leucine was produced by coupled enzyme reactions using ω-transaminase derived from *Ochrobactrum anthropi* and using isopropylamine.

L-tert-Leucine was produced by conducting reactions at 37° C. for 30 or 40 hours using 1 mL of a mixture of 20 mM trimethylpyruvate, 4 mM D/L-homoalanine, 25 mM isopropylamine, 0.1 mM PLP, 50 mM potassium phosphate (pH 7), 0.6 U/mL branched-chain transaminase and 4.8 U/mL ω-transaminase. The result is shown [Table 9].

TABLE 9

| Reaction time (hr) | Concentration (mM) | |
| --- | --- | --- |
| | 30 | 40 |
| Trimethylpyruvate | 3.621 | |
| L-Homoalanine | 1.907 | 1.615 |
| 2-Oxobutyrate | 0.008 | |
| L-tert-Leucine | 14.912 | 18.225 |
| Isopropylamine | 11.213 | 10.600 |

Example 23

Figure 16:
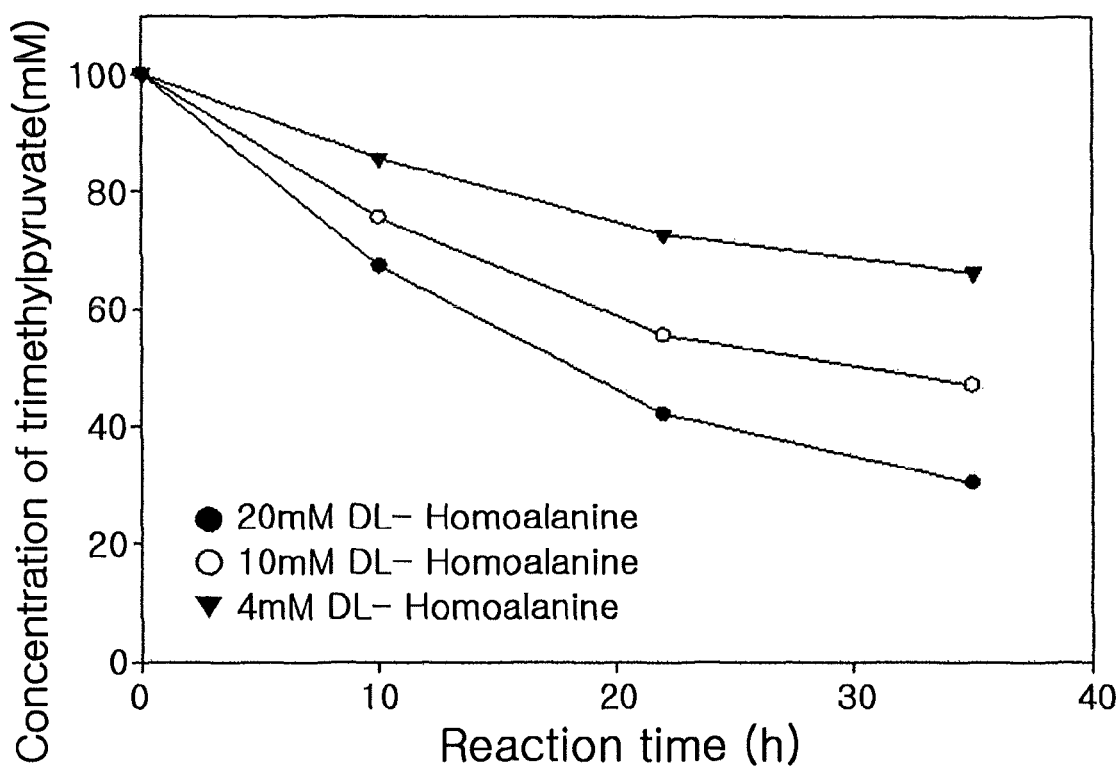
FIG. 16 shows a result of producing L-tert-leucine at high concentration through coupled enzyme reactions using trimethylpyruvate at high concentration according to an exemplary embodiment of the present disclosure.

Production of High-Concentration L-tert-leucine by Coupled Enzyme Reactions Using High-Concentration Trimethylpyruvate High-concentration L-tert-leucine was produced by conducting reactions using high-concentration trimethylpyruvate, ω-transaminase derived from *Ochrobactrum anthropi* and isopropylamine. The conversion from trimethylpyruvate to L-tert-leucine was confirmed by conducting reactions at 37° C. using 100 mM trimethylpyruvate, 4, 10 or 20 mM D/L-homoalanine, 125 mM isopropylamine, 0.1 mM PLP, 50 mM potassium phosphate (pH 7), 0.6 U/mL branched-chain transaminase and 20 U/mL ω-transaminase. The result is shown in FIG. 16 and [Table 10].

TABLE 10

| Concentration (mM) after reaction for 10 hours using 20 mM cosubstrate | | | | |
| --- | --- | --- | --- | --- |
| L-tert-Leucine | Trimethyl-pyruvate | L-Homoalanine | 2-Oxobutyrate | Isopropylamine |
| 39.963 | 67.331 | 10.548 | 0.350 | 106.357 |

Example 24

Production of Various High-Concentration L-amino Acids by Coupled Enzyme Reactions Various high-concentration unnatural amino acids were produced by coupled enzyme reactions. Unnatural amino acids were produced by conducting reactions at 37° C. using 100 mM keto acid, 5 mM L-homoalanine, 150 mM isopropylamine, 0.5 mM PLP, 50 mM potassium phosphate (pH 7), 20 U/mL branched-chain transaminase and 50 U/mL ω-transaminase.

As keto acids for the production of the optically active amino acids, trimethylpyruvate was used for L-tert-leucine, 2-oxopentanoate for L-norvaline, 2-oxohexanoate for L-norleucine, 2-(3-hydroxy-1-adamantyl)-2-oxoethanoic acid for L-3-hydroxyadamantylglycine, 2-oxooctanoic acid for L-2-aminocaprylic acid, and phenylglyoxylate for L-phenylglycine. The various unnatural amino acids were produced by the coupled enzyme reactions with a conversion rate of 93% or higher. The result is shown in [Table 11].

TABLE 11

| Reaction time (hr) | Conversion rate (%) | Unnatural L-amino acids (% ee) |
| --- | --- | --- |
| 18 | 94 | L-tert-Leucine (>99.9) |
| 9 | 99 | L-Norvaline (>99.9) |
| 9 | 97 | L-Norleucine (>99.9) |
| 5 | 98 | L-2-Caprylic acid (>99.9) |
| 12 | 93 | L-Hydroxy-adamantyl-glycine (>99.9) |
| 12 | 95 | L-Phenylglycine (>99.9) |

L-tert-Leucine was produced with a conversion of 97% by conducting reactions using 50 mL of a mixture of 0.3 M trimethylpyruvate, 20 mM L-homoalanine, 0.45 M isopropylamine, 0.5 mM PLP, 50 mM phosphate pH 8, 35 U/mL BCTA and 30 U/mL OATA. 1.365 g of pure L-tert-leucine was obtained through purification based on solubility.

Example 25

Production of Various High-Concentration D-amino Acids by Coupled Enzyme Reactions Various high-concentration unnatural D-amino acids were produced by coupled enzyme reactions by D-amino-acid transaminase and (R)-selective ω-transaminase. Unnatural amino acids were produced by conducting reactions at 37° C. using 100 mM keto acid, 5 mM D-alanine, 150 mM isopropylamine, 0.5 mM PLP, 50 mM potassium phosphate (pH 7), 5 U/mL D-amino-acid transaminase and 50 U/mL (R)-selective ω-transaminase derived from *Arthrobacter* species.

As keto acids for the production of the optically active amino acids, 2-oxopentanoate was used for D-norvaline, 2-oxohexanoate for D-norleucine, and phenylglyoxylate for D-phenylglycine. The various unnatural amino acids were produced by the coupled enzyme reactions with a conversion rate of 93% or higher. The result is shown in [Table 12].

TABLE 12

| Reaction time (hr) | Conversion rate (%) | Unnatural D-amino acids (% ee) |
| --- | --- | --- |
| 3 | 98 | D-Norvaline (>99.9) |
| 7 | 96 | D-Valine (>99.9) |
| 5 | 96 | D-Norleucine (>99.9) |
| 7 | 99 | D-Leucine (>99.9) |
| 5 | 99 | D-Glutamate (>99.9) |
| 15 | 97 | D-Phenylglycine (>99.9) |
| 3 | 99 | D-Phenylalanine (>99.9) |

D-phenylglycine was produced with a conversion of 98% by conducting reactions using 50 mL of a mixture of 0.3 M phenylformate, 20 mM D-alanine, 0.45 M isopropylamine, 0.5 mM PLP, 50 mM phosphate pH 8, 35 U/mL DATA and 30

U/mL ARmutTA. 2.02 g of pure D-phenylglycine was obtained through purification based on solubility.

INDUSTRIAL APPLICABILITY

The present disclosure allows production of various optically active amino acids with high purity and high efficiency by solving the low equilibrium constant problem of transaminase and is applicable to production of various optically active amino acids in industrial scale. Since the present disclosure allows easy production of various unnatural amino acids having high reactivity and stability, which are used as pharmaceutical precursors, it can be usefully employed in preparation of pharmaceuticals, food additives and various animal feeds.

The invention claimed is:

1. A method for preparing an optically active amino acid by a cascade reaction, comprising:
   (A) converting a keto acid to an amino acid substrate and an amino acid cosubstrate by alpha transaminase wherein the amino acid cosubstrate is converted into a keto acid of the amino acid substrate; and
   (B) transferring an amino group of an amine substrate to the keto acid of the amino acid cosubstrate by ω-transaminase (ω-TA), and generating the amino acid cosubstrate, wherein the amine substrate is isopropylamine and the cascade reaction produces an optically active amino acid.

2. The method for preparing an optically active amino acid according to claim 1, wherein the amino acid cosubstrate is an amino acid showing reactivity for both α-transaminase and ω-transaminase (ω-TA).

3. The method for preparing an optically active amino acid according to claim 1, wherein the keto acid is selected from pyruvate, 2-oxobutyrate, 2-(3-hydroxy-1-adamantyl)-2-oxoethanoic acid, trimethylpyruvate, 3-methyl-2-oxobutyrate, 3-methyl-2oxopentanoic acid, 4-methyl-2-oxopentanoic acid, 2-oxopentanoic acid, 2-oxohexanoic acid, 2-oxooctanoic acid, fluoropyruvate, hydroxypyruvate, mercaptopyruvate, oxaloacetate, ketoglutarate, phenylglyoxylate, phenylpyruvate, 4-hydroxyphenylglyoxylate, 4-dimethyl-2oxopentanoic acid, 3-dimethyl-2-oxopentanoic acid, 3-ethyl-3-methyl-2-oxopentanoic acid and 5-dimethyl-2-oxohexanoic acid.

4. The method for preparing an optically active amino acid according to claim 1, wherein the amine substrate is selected from benzylamine, methylbenzylamine, ethylbenzylamine, isopropylamine, 2-butylamine, 1-aminoindane, cyclopropylethylamine, 2-aminopentane, 3-methyl-2-butylamine, 1,3-dimethylbutylamine, 2-aminooctane, 1-methoxy-2-propylamine, 2-aminohexane, p-fluoromethylbenzylamine, mexiletine and 1-methyl-3-phenylpropylamine.

5. The method for preparing an optically active amino acid according to claim 1, wherein the optically active amino acid is selected from alanine, homoalanine, norvaline, norleucine, 2-aminocaprylic acid, valine, leucine, isoleucine, tert-leucine, fluoroalanine, serine, cysteine, aspartate, glutamate, phenylglycine, phenylalanine, 4-hydroxyphenylalanine, 3-hydroxyadamantylglycine, neopentylglycine, 3-dimethyl-2-aminopentanoic acid, 3-ethyl-3-methyl-2-aminopentanoic acid and 5-dimethyl-2-aminohexanoic acid in L- or D-form.

6. The method for preparing an optically active amino acid according to claim 1, wherein the α-transaminase is branched-chain transaminase (BCTA), D-amino-acid transaminase (DATA), aromatic-amino-acid transaminase (AroTA), aspartate transaminase (AspTA) or alanine transaminase (ATA) and the ω-transaminase is one isolated from *Paracoccus denitrificans*, *Ochrobactrum anthropic* or *Arthrobacter* species.

7. The method for preparing an optically active amino acid according to claim 1, wherein, in the cascade reaction, the concentration of the amino acid cosubstrate is 0.1-20% of the concentration of the keto acid substrate.

8. The method for preparing an optically active amino acid according to claim 1, wherein the cascade reaction is conducted by further adding an organic solvent if the reactivity of the ω-transaminase is inhibited by a ketone or an aldehyde.

* * * * *

SEQUENCE LISTING

```
<160> NUMBER OF SEQ ID NOS: 12

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atcatggaat tcatgaccac gaagaaagct                                        30

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aaaaactcga gttattgatt aacttgatct aacca                                  35

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gatatacata tgaaccaacc gcaaagc                                           27

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtggtgctcg agggccacct cggcaaa                                           27

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, t, g, unknown or other

<400> SEQUENCE: 5
```

```
gatataccat ggnnactgct cagccaaact ct                                    32
```

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
cgagtgcggc cgtcctggtg aggcttgc                                         28
```

<210> SEQ ID NO 7
<211> LENGTH: 930
<212> TYPE: DNA
<213> ORGANISM: Escherichia coli

<400> SEQUENCE: 7

```
atgaccacga agaaagctga ttacatttgg ttcaatgggg agatggttcg ctgggaagac      60
gcgaaggtgc atgtgatgtc gcacgcgctg cactatggca cttcggtttt tgaaggcatc    120
cgttgctacg actcgcacaa aggaccggtt gtattccgcc atcgtgagca tatgcagcgt    180
ctgcatgact ccgccaaaat ctatcgcttc ccggtttcgc agagcattga tgagctgatg    240
gaagcttgtc gtgacgtgat ccgcaaaaac aatctcacca cgcctatat ccgtccgctg    300
atcttcgtcg gtgatgttgg catgggagta aacccgccag cgggatactc aaccgacgtg    360
attatcgctg cttccgtg gggagcgtat ctgggcgcag aagcgctgga gcaggggatc      420
gatgcgatgg tttcctcctg aaccgcgca gcaccaaaca ccatcccgac ggcggcaaaa    480
gccggtggta actacctctc ttccctgctg gtgggtagcg aagcgcgccg ccacggttat    540
caggaaggta tcgcgctgga tgtgaacggt tatatctctg aaggcgcagg cgaaaacctg    600
tttgaagtga agatggtgt gctgttcacc ccaccgttca cctcctccgc gctgccgggt    660
attacccgtg atgccatcat caaactggcg aaagagctgg gaattgaagt acgtgagcag    720
gtgctgtcgc gcgaatccct gtacctggcg gatgaagtgt ttatgtccgg tacgcggca    780
gaaatcacgc cagtgcgcag cgtagacggt attcaggttg gcgaaggccg ttgtggcccg    840
gttaccaaac gcattcagca agccttcttc ggcctcttca ctggcgaaac cgaagataaa    900
tggggctggt tagatcaagt taatcaataa                                     930
```

<210> SEQ ID NO 8
<211> LENGTH: 309
<212> TYPE: PRT
<213> ORGANISM: Escherichia coli

<400> SEQUENCE: 8

Met Thr Thr Lys Lys Ala Asp Tyr Ile Trp Phe Asn Gly Glu Met Val
1               5                   10                  15

Arg Trp Glu Asp Ala Lys Val His Val Met Ser His Ala Leu His Tyr
                20                  25                  30

Gly Thr Ser Val Phe Glu Gly Ile Arg Cys Tyr Asp Ser His Lys Gly
            35                  40                  45

Pro Val Val Phe Arg His Arg Glu His Met Gln Arg Leu His Asp Ser
        50                  55                  60

Ala Lys Ile Tyr Arg Phe Pro Val Ser Gln Ser Ile Asp Glu Leu Met
65                  70                  75                  80

```
Glu Ala Cys Arg Asp Val Ile Arg Lys Asn Asn Leu Thr Ser Ala Tyr
                85                  90                  95

Ile Arg Pro Leu Ile Phe Val Gly Asp Val Gly Met Gly Val Asn Pro
            100                 105                 110

Pro Ala Gly Tyr Ser Thr Asp Val Ile Ala Ala Phe Pro Trp Gly
            115                 120                 125

Ala Tyr Leu Gly Ala Glu Ala Leu Glu Gln Gly Ile Asp Ala Met Val
        130                 135                 140

Ser Ser Trp Asn Arg Ala Ala Pro Asn Thr Ile Pro Thr Ala Ala Lys
145                 150                 155                 160

Ala Gly Gly Asn Tyr Leu Ser Ser Leu Leu Val Gly Ser Glu Ala Arg
                165                 170                 175

Arg His Gly Tyr Gln Glu Gly Ile Ala Leu Asp Val Asn Gly Tyr Ile
                180                 185                 190

Ser Glu Gly Ala Gly Glu Asn Leu Phe Glu Val Lys Asp Gly Val Leu
            195                 200                 205

Phe Thr Pro Pro Phe Thr Ser Ser Ala Leu Pro Gly Ile Thr Arg Asp
    210                 215                 220

Ala Ile Ile Lys Leu Ala Lys Glu Leu Gly Ile Glu Val Arg Glu Gln
225                 230                 235                 240

Val Leu Ser Arg Glu Ser Leu Tyr Leu Ala Asp Glu Val Phe Met Ser
                245                 250                 255

Gly Thr Ala Ala Glu Ile Thr Pro Val Arg Ser Val Asp Gly Ile Gln
            260                 265                 270

Val Gly Glu Gly Arg Cys Gly Pro Val Thr Lys Arg Ile Gln Gln Ala
        275                 280                 285

Phe Phe Gly Leu Phe Thr Gly Glu Thr Glu Asp Lys Trp Gly Trp Leu
    290                 295                 300

Asp Gln Val Asn Gln
305

<210> SEQ ID NO 9
<211> LENGTH: 1362
<212> TYPE: DNA
<213> ORGANISM: Paracoccus denitrificans

<400> SEQUENCE: 9
atgaaccaac cgcaaagctg ggaagcccgg gccgagacct attcgctcta cggtttcacc      60
gacatgccct cggtccatca gcggggcacg gtcgtcgtga cccatggcga ggggccctat     120
atcgtcgatg tccatggccg ccgctatctg gatgccaatt cgggcctgtg aacatggtc     180 gcgggcttcg accacaaggg cctgatcgag ccgccaaggg cgcaatacga ccgctttccc     240
ggctatcacg cctttttcgg ccgcatgtcc gaccagacct gatgctgtc ggaaaagctg     300 gtcgaggtct cgccattcga acaggcccgg gtcttctata ccaattccgg ctccgaggcg     360
aacgacacca tggtcaagat gctgtggttc ctgcatgccg ccgagggcaa gccgcaaaag     420
cgcaagatcc tgacgcgctg gaacgcctat acggcgtga ccgcggtttc ggcctcgatg     480
accggcaagc cctacaactc ggtcttcggc ctgccgctgc ccggcttcat ccacctgacc     540
tgcccgcatt actggcgcta tggcgaggaa ggcgagaccc aggcgcaatt cgtcgcccgc     600
ctggcacgcg agcttgagga taccatcacc gcgagggcg ccgacaccat cgccggcttc     660
ttcgccgagc cggtgatggg cgcggggggg gtgatcccgc cggcgaaggg ttatttccag     720
gccatcctgc cgatcttgcg caagtatgac atcccgatga tctcggacga ggtgatctgc     780
```

```
ggcttcgggc gcaccggcaa cacctggggc tgcctgacct acgacttcat gcccgatgcg    840
atcatctcgt ccaagaacct gactgcgggc ttcttcccga tgggcgccgt catcctcggg    900
cccgacctcg ccaagcgggt cgaggccgcg gtcgaggcga tcgaggagtt cccgcacggc    960
ttcaccgcct cgggccatcc ggtcggctgc gccatcgcgc tgaaggccat cgacgtggtg   1020
atgaacgagg ggctggccga gaatgtccgc cgcctcgcac cccgcttcga ggcggggctg   1080
aagcgcatcg ccgaccgccc gaacatcggc gaataccgcg catcggcctt catgtgggcg   1140
ctggaggcgg tcaaggacaa gccgaccaag accccttcg acgccaatct ttcggtcagc   1200
gagcgcatcg ccaatacctg caccgatctg gggctgatct gccggccgct gggccagtcc   1260
atcgtgctgt gcccgccctt catcctgacc gaggcgcaga tggacgagat gttcgaaaag   1320
ctggaaaagg cgctcgacaa ggtctttgcc gaggtggcct ga                      1362
```

<210> SEQ ID NO 10
<211> LENGTH: 453
<212> TYPE: PRT
<213> ORGANISM: Paracoccus denitrificans

<400> SEQUENCE: 10

```
Met Asn Gln Pro Gln Ser Trp Glu Ala Arg Ala Glu Thr Tyr Ser Leu
1               5                   10                  15

Tyr Gly Phe Thr Asp Met Pro Ser Val His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Glu Ala Lys Ala Gln Tyr Asp Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Asn Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Ile His Leu Thr Cys Pro His Tyr Trp Arg Tyr Gly Glu Glu Gly Glu
            180                 185                 190

Thr Glu Ala Gln Phe Val Ala Arg Leu Ala Arg Glu Leu Glu Asp Thr
        195                 200                 205

Ile Thr Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Met Ile Ser Asp
                245                 250                 255

Glu Val Ile Cys Gly Phe Gly Arg Thr Gly Asn Thr Trp Gly Cys Leu
            260                 265                 270
```

```
Thr Tyr Asp Phe Met Pro Asp Ala Ile Ile Ser Ser Lys Asn Leu Thr
            275                 280                 285

Ala Gly Phe Phe Pro Met Gly Ala Val Ile Leu Gly Pro Asp Leu Ala
        290                 295                 300

Lys Arg Val Glu Ala Ala Val Glu Ala Ile Glu Glu Phe Pro His Gly
305                 310                 315                 320

Phe Thr Ala Ser Gly His Pro Val Gly Cys Ala Ile Ala Leu Lys Ala
            325                 330                 335

Ile Asp Val Val Met Asn Glu Gly Leu Ala Glu Asn Val Arg Arg Leu
        340                 345                 350

Ala Pro Arg Phe Glu Ala Gly Leu Lys Arg Ile Ala Asp Arg Pro Asn
    355                 360                 365

Ile Gly Glu Tyr Arg Gly Ile Gly Phe Met Trp Ala Leu Glu Ala Val
370                 375                 380

Lys Asp Lys Pro Thr Lys Thr Pro Phe Asp Ala Asn Leu Ser Val Ser
385                 390                 395                 400

Glu Arg Ile Ala Asn Thr Cys Thr Asp Leu Gly Leu Ile Cys Arg Pro
            405                 410                 415

Leu Gly Gln Ser Ile Val Leu Cys Pro Pro Phe Ile Leu Thr Glu Ala
        420                 425                 430

Gln Met Asp Glu Met Phe Glu Lys Leu Glu Lys Ala Leu Asp Lys Val
    435                 440                 445

Phe Ala Glu Val Ala
    450
```

<210> SEQ ID NO 11
<211> LENGTH: 1371
<212> TYPE: DNA
<213> ORGANISM: Ochrobactrum anthropi

<400> SEQUENCE: 11

```
atgactgctc agccaaactc tcttgaagct cgcgatatcc gttatcatct ccattcttat     60
accgatgctg tccgcctcga agcggaaggt ccgctcgtca tcgagcgtgg cgatggcatt    120
tacgtcgaag atgtatcggg caagcgctat atcgaagcga tgtcaggact gtggagtgtt    180
ggcgtgggct tttccgaacc gcgtctggcc gaagcagctg cacgacagat gaagaagctg    240
cctttctacc atacattctc ctaccgttcg catggtcctg tcattgatct ggcagaaaag    300
cttgtctcaa tggctcctgt tccgatgagc aaggcctact caccaattca aggttccgaa    360
gccaacgata cggtcgtcaa gttgatctgg tatcgctcca atgcgctggg tgaaccggag    420
cgcaagaaaa tcatctcacg caagcgcggc tatcacggtg tgacgattgc ctctgccagc    480
ctgaccggct tgcccaacaa tcaccgttct ttcgatctgc cgatcgatcg tatcctgcat    540
acgggctgcc gcatttttta cgcgaaggca caggctggcg agagtgagga acaattcgca    600
acgcggctgg cggatgagct ggaacagttg atcatcgcgg aagtcctcca ccatcgct     660
gctttcattg gcgagccggt gatggggct ggcggcgtag tcgtgccgcc caaaacctat    720
tgggaaaaag tgcaggctgt tctcaagcgc tacgatattc tgctgatcgc cgacgaggtt    780
atttgcggct cggacggac aggcaatctg ttcggcagcc agactttcga tatgaaaccg    840
gacattctgg tgatgtcgaa gcagctttcg tcatcctatc tgccgatttc ggccttcctc    900
atcaacgagc gtgtgtacgc gccaattgcc gaagaaagcc acaagatcgg cacgcttggc    960
acgggcttca cggcatctgg ccatccggtg gcggcagcgg tagcgctgga aaacctcgcc   1020
attattgaag agcgtgatct ggtcgccaat gcgcgcgacc gcggcaccta tgcagaag    1080
```

```
cgcctgcgtg agttgcagga tcatcctctg gtcggcgaag tgcgtggcgt tggtctcata    1140
gccggtgtcg agcttgtcac cgacaagcag gccaagacgg gccttgaacc aaccggcgct    1200
ctgggcgcaa aggcaaacgc cgttcttcag gagcgcggcg tcatttcccg cgcaatgggc    1260
gatacgcttg ccttctgccc gccgctcatc atcaacgatc agcaggttga tacgatggtg    1320
tccgcgctcg aggcgacgct gaacgatgtt caggcaagcc tcaccaggta a             1371
```

<210> SEQ ID NO 12
<211> LENGTH: 456
<212> TYPE: PRT
<213> ORGANISM: Ochrobactrum anthropi

<400> SEQUENCE: 12

```
Met Thr Ala Gln Pro Asn Ser Leu Glu Ala Arg Asp Ile Arg Tyr His
1               5                   10                  15

Leu His Ser Tyr Thr Asp Ala Val Arg Leu Glu Ala Glu Gly Pro Leu
            20                  25                  30

Val Ile Glu Arg Gly Asp Gly Ile Tyr Val Glu Asp Val Ser Gly Lys
        35                  40                  45

Arg Tyr Ile Glu Ala Met Ser Gly Leu Trp Ser Val Gly Val Gly Phe
    50                  55                  60

Ser Glu Pro Arg Leu Ala Glu Ala Ala Arg Gln Met Lys Lys Leu
65                  70                  75                  80

Pro Phe Tyr His Thr Phe Ser Tyr Arg Ser His Gly Pro Val Ile Asp
                85                  90                  95

Leu Ala Glu Lys Leu Val Ser Met Ala Pro Val Pro Met Ser Lys Ala
            100                 105                 110

Tyr Phe Thr Asn Ser Gly Ser Glu Ala Asn Asp Thr Val Val Lys Leu
        115                 120                 125

Ile Trp Tyr Arg Ser Asn Ala Leu Gly Glu Pro Glu Arg Lys Lys Ile
    130                 135                 140

Ile Ser Arg Lys Arg Gly Tyr His Gly Val Thr Ile Ala Ser Ala Ser
145                 150                 155                 160

Leu Thr Gly Leu Pro Asn Asn His Arg Ser Phe Asp Leu Pro Ile Asp
                165                 170                 175

Arg Ile Leu His Thr Gly Cys Pro His Phe Tyr Arg Glu Gly Gln Ala
            180                 185                 190

Gly Glu Ser Glu Glu Gln Phe Ala Thr Arg Leu Ala Asp Glu Leu Glu
        195                 200                 205

Gln Leu Ile Ile Ala Glu Gly Pro His Thr Ile Ala Ala Phe Ile Gly
    210                 215                 220

Glu Pro Val Met Gly Ala Gly Val Val Pro Pro Lys Thr Tyr
225                 230                 235                 240

Trp Glu Lys Val Gln Ala Val Leu Lys Arg Tyr Asp Ile Leu Leu Ile
                245                 250                 255

Ala Asp Glu Val Ile Cys Gly Phe Gly Arg Thr Gly Asn Leu Phe Gly
            260                 265                 270

Ser Gln Thr Phe Asp Met Lys Pro Asp Ile Leu Val Met Ser Lys Gln
        275                 280                 285

Leu Ser Ser Ser Tyr Leu Pro Ile Ser Ala Phe Leu Ile Asn Glu Arg
    290                 295                 300

Val Tyr Ala Pro Ile Ala Glu Glu Ser His Lys Ile Gly Thr Leu Gly
305                 310                 315                 320
```

```
Thr Gly Phe Thr Ala Ser Gly His Pro Val Ala Ala Val Ala Leu
            325             330             335
Glu Asn Leu Ala Ile Ile Glu Glu Arg Asp Leu Val Ala Asn Ala Arg
            340             345             350
Asp Arg Gly Thr Tyr Met Gln Lys Arg Leu Arg Glu Leu Gln Asp His
            355             360             365
Pro Leu Val Gly Glu Val Arg Gly Val Gly Leu Ile Ala Gly Val Glu
        370             375             380
Leu Val Thr Asp Lys Gln Ala Lys Thr Gly Leu Glu Pro Thr Gly Ala
385             390             395             400
Leu Gly Ala Lys Ala Asn Ala Val Leu Gln Glu Arg Gly Val Ile Ser
            405             410             415
Arg Ala Met Gly Asp Thr Leu Ala Phe Cys Pro Pro Leu Ile Ile Asn
            420             425             430
Asp Gln Gln Val Asp Thr Met Val Ser Ala Leu Glu Ala Thr Leu Asn
        435             440             445
Asp Val Gln Ala Ser Leu Thr Arg
450             455
```